United States Patent [19]

Tsuji et al.

[11] 4,440,683

[45] Apr. 3, 1984

[54] CYCLIZATION TO FORM CEPHEM RING AND AZETIDINONE INTERMEDIATES THEREFOR

[75] Inventors: Teruji Tsuji, Osaka; Yoshio Hahashima, Kyoto; Mitsuru Yoshioka, Osaka; Masayuki Narisada, Osaka; Hiroshi Tanida, Osaka; Taichiro Komeno, Osaka; Wataru Nagata, Hyogo, all of Japan

[73] Assignee: Shionogi & Co., Ltd., Osaka, Japan

[21] Appl. No.: 338,651

[22] Filed: Jan. 11, 1982

Related U.S. Application Data

[60] Division of Ser. No. 125,232, Feb. 27, 1980, Pat. No. 4,332,722, which is a division of Ser. No. 66,462, Aug. 13, 1979, abandoned, which is a continuation of Ser. No. 856,807, Dec. 1, 1977, abandoned, which is a division of Ser. No. 658,665, Feb. 17, 1976, Pat. No. 4,079,181.

[30] Foreign Application Priority Data

| Feb. 17, 1975 [JP] | Japan | 50/19612 |
| Feb. 21, 1975 [JP] | Japan | 50/22229 |
| Mar. 7, 1975 [JP] | Japan | 50/28452 |
| Mar. 30, 1975 [JP] | Japan | 50/33808 |

[51] Int. Cl.³ .................. C07D 205/08; C07D 403/04; C07D 401/12; C07D 405/12
[52] U.S. Cl. .................. 260/239 A; 260/245.4; 260/330.3; 260/330.9; 544/182; 544/215; 544/238; 544/335; 544/336; 546/275

[58] Field of Search ............ 260/245.4, 239 A, 330.3; 546/275; 544/238, 335, 336, 182, 215

[56] References Cited

U.S. PATENT DOCUMENTS

| 4,130,557 | 12/1978 | Hamashima | 260/239 A |
| 4,147,864 | 4/1979 | Woodward | 260/239 A |
| 4,206,120 | 6/1980 | Hunt | 260/239 A |
| 4,264,597 | 4/1981 | Hashimoto | 260/239 A |

Primary Examiner—Mark L. Berch
Attorney, Agent, or Firm—Wenderoth, Lind & Ponack

[57] ABSTRACT

An intermediate represented by following formula for synthesizing 3-hydroxy-3-cephem compounds.

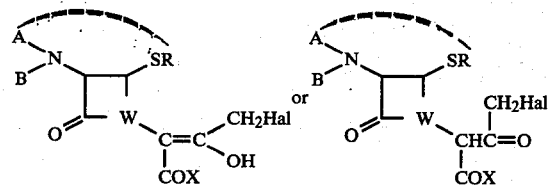

wherein A and B each is a hydrogen or amine substituent; R is a hydrogen or thiol substituent; Nal is a halogen; X is a hydroxy or carboxy protecting group; the broken line between A and R shows that when R and B are hydrogens, and A is a carboxylic acyl, the substituents can be combined to form an azetidimethiazoline bicyclic ring; and the enamine derivatives thereof.

6 Claims, No Drawings

CYCLIZATION TO FORM CEPHEM RING AND AZETIDINONE INTERMEDIATES THEREFOR

This application is a division of application Ser. No. 125,232, filed Feb. 27, 1980, now U.S. Pat. No. 4,332,722 which application is a division of application Ser. No. 66,462, filed Aug. 13, 1979 (now abandoned), which application is a continuation of application Ser. No. 856,807, filed Dec. 1, 1977 (now abandoned), which application is in turn a division of application Ser. No. 658,665, filed Feb. 17, 1976 (now U.S. Pat. No. 4,079,181).

This invention relates to cyclization to form the cephem ring, and the intermediates therefor. More specifically, it relates to compounds represented by following formula

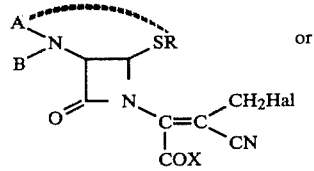

wherein A and B each is a hydrogen or amine substituent; R is a hydrogen or thiol substituent; Hal is a halogen; X is a hydroxy or a carboxy protecting group; the broken line shows that when R and B are hydrogens and A is a carboxylic acyl, the substituents can be combined to form an azetidinothiazoline bicyclic ring; and their enamine derivatives, and to the processes for the cyclization to form cephem ring through the said intermediates shown above by the reactions representable by following reaction scheme:

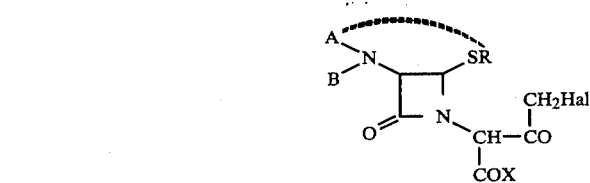

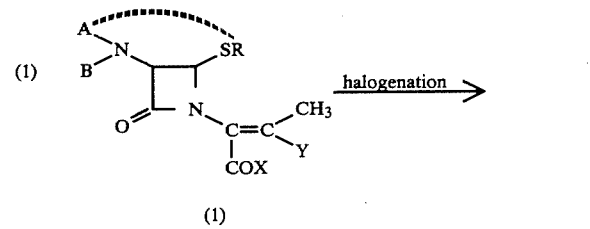

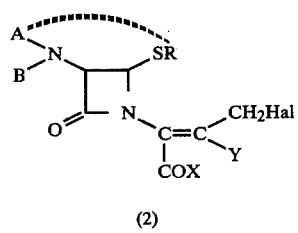

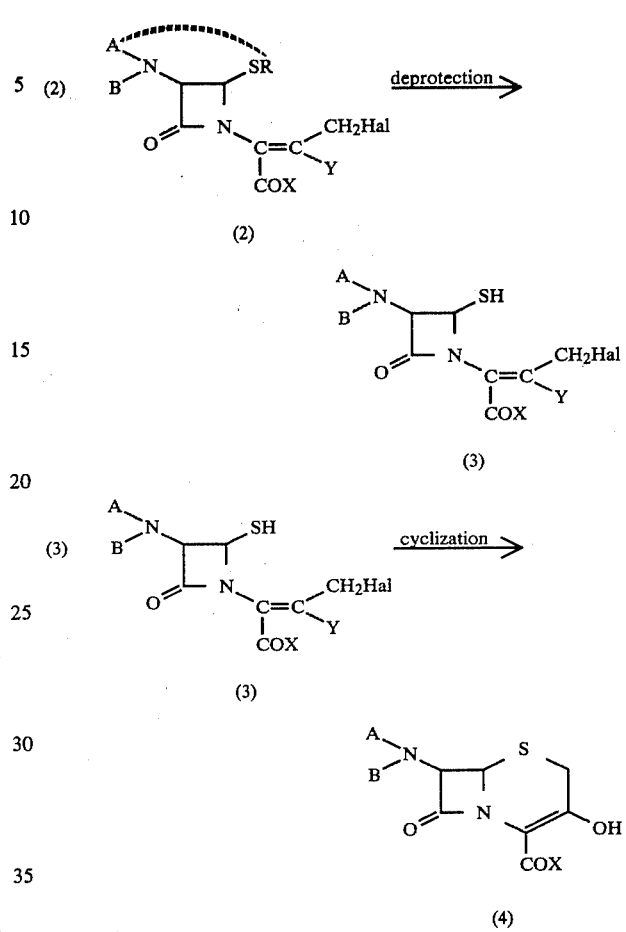

wherein A, B, R, Nal, X and the broken line are as defined above; and Y is a hydroxy or enamine group. When Y is ON, it can be in one form.

Many trials for synthesizing 3-cephem ring in large scale have been reported, but no factory produces cephalosporine by synthesizing the nucleus except for cephalexin. This invention provides mild cyclization to form 3-hydroxy-3-cephem compounds through 4-mercaptoazetidinone derivatives.

Efforts to cyclize a type of compounds of the formula (2) or (3) where Y is ether than hydroxy or a substituted amine resulted in unsatisfactory results. However, when Y is a group which promotes enolization to form a double bond toward the exo-postion, the cyclization took place smoothly to form the objective 3-hydroxy-3-cephem compound (4).

The 3-hydroxy-3-cephem compound (4) are useful intermediates for synthesizing useful cephem compounds (e.g. recently developed 3-methoxy-7-(α-phenylglycinamido)-3-cephem-4-carboxylic acid, 3-chloro-7-(α-phenylglycinamido)-3-cephem-4-carboxylic acid, 3-bromo-7-(2-thienylacetamido)-3-cephem-4-carboxylic acid).

In the above reaction scheme, the ABN group is an amino or substituted amine. The said substituted amino can be acylamino, hydrocarbylamino, hydrocarbylideneamino, silylamino, sulfamylamino, or like conventional protecting groups containing up to 20 carbon atoms. Such groups are conventional in the field of cephalosporin or penicillin chemistry.

Representative acyls in the said acylamine include inorganic acyls such as carbonic acyl (e.g. alkoxycarbonyl, aralkoxycarbonyl or aryloxycarbonyl), sulfuric acyl, phosphoric acyl (e.g. dialkoxyphosphinyl, dialkoxythiophosphonyl or alkoxyaminophosphoroyl); and organic acyls such as alkanoyl, cycloalkanoyl aralkanoyl, arayl, alkylsulfonyl, arylsulfonyl or alkylphosphenyl. These groups can, where possible, be interrupted by a hetero atom in their skeleton or can be unsaturated or substituted by, for example, halogen (e.g. fluorine, chlorine, or bromine), nitrogen function (e.g. amine, hydrazine, azide, alkylamine, arylamine, acylamine, akylideneamine, acylimine, imine or nitro), oxygen function (e.g. hydroxy, alkoxy, aralkoxy, aryloxy, acyloxy or exe), sulfur function(e.g. mercapto, alkylthio, aralkylthio, arylthio, acylthio, thioxo, sulfo, sulfonyl, sulfinyl alkoxy-sulfonyl, or aryloxysulfinyl), carbon function (e.g. alkyl, alkenyl, aralkyl, aryl, carboxy, carbalkoxy, carbamoyl, alkanoyl, aroyl, aminoalkyl, aralkanoyl or cyano), or phosphorous function (e.g. phospho or phosphoroyl). A and B can also be considered together as forming a diacyl group of a polybasic acid (e.g. phthaloyl, pyridine-2,3-dicarbonyl, maleoyl or succinoyl).

More preferable groups in the said acyl can be the acyls of penicillin side chain (e.g. phenylacetyl, phenoxyacetyl, heptanoyl), or these convertible to a group profitable for the antibacterial activity of the end products (e.g. hydrogen, N-tertiary butoxy-2-phenylglycinamido, α-(1-carbomethoxy-1-isopropen-2-yl)amino-z-phenylglycyl, 4-phenyl-2,2-dimethyl-5-exe-1,3- imidazolidin-1-yl, α-diphenylmethoxycarbonyl-z-phenylacetamido).

The hydrocarbon groups which may be represented by A and/or B can be easily removable aliphatic hydrocarbon groups containing from 1 to 20 carbon atoms (e.g. alkyl, alkenyl, aralkyl or ether aliphatic hydrocarbon groups) or easily removable mono-cyclic aromatic hydrocarbon groups (e.g. phenyl or pyrimidyl). These groups can, where possible, be interrupted by a hetero atom in the skeleton thereof or can be unsaturated or substituted by a substituent (e.g. halogen atom or nitrogen, oxygen, sulfur, carbon or phosphorous functions). A and B can also be considered together as forming a divalent hydrocarbon group (e.g. alkylene, aralkylene, alkylidene, aralkylidene, α-halo- or alkoxy-aralkylidene, diarylmethylidene or cycloalkylidene), which can, where possible, be interrupted by a hetero atom in the skeleton thereof or can be substituted by a substituent as cited above or can be unsaturated.

When group A is acyl and group B is a hydrocarbon, they can be combined together with the nitrogen atom bound to position 7 of the cephem ring to form a cyclic group (e.g. a 4-oxo-3-imidazolidinyl ring).

The silyl (e.g. trialkylsilyl) and sulfonyl (e.g. phenylsulfonyl or o-nitrophenylsulfonyl) groups which may be represented by A and/or B are conventional amine protecting groups.

Representative acyl groups for A and B in the above formula (I) include following groups:
(1) alkanoyl containing from 1 to 5 carbon atoms;
(2) haloalkanoyl containing from 2 to 5 carbon atoms;
P0 (3) azidoacetyl;
(4) cyanoacetyl;
(5) acyl groups of the formula:

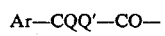

in which Q and Q' are each hydrogen or methyl; and Ar is phenyl, dihydrophenyl or a monocyclic heterocyclic aromatic group containing from 1 to 4 hetero atoms selected from nitrogen, oxygen and/or sulfur atoms, and may optionally be substituted by an inert group e.g. an alkyl or alkoxy group containing from 1 to 3 carbon atoms, chlorine, bromine, iodine, fluorine, trifluoromethyl, hydroxy, cyano, aminomethyl, amino or nitro;
(6) acyl groups of the formula:

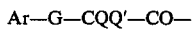

in which G is an oxygen or sulfur; and A-, Q, and Q' are as defined above;
(7) acyl groups of the formula:

in which Ar is as defined above; and T is (i) amino, ammonium, amino substituted by such conventional amino-protecting groups as benzyloxycarbonyl, alkoxycarbonyl containing from 1 to 4 carbon atoms, cyclopentyloxycarbonyl, cyclohexyloxycarbonyl, benzhydryloxycarbonyl, cyclopropylmethoxycarbonyl, methanesulfonylethoxycarbonyl, triphenylmethyl, 2,2,2-trichloroethoxycarbonyl, guanidylcarbamoyl, optionally substituted ureido carbonyl including 3-methanesulfonylimidazolidon-1-ylcarbonyl, alkanoyl containing from 1 to 5 carbon atoms, pyrenecarbonyl, thiopyrenecarbonyl, pyridenecarbonyl, homo- or hetero-cyclic mome-cyclic aromaic acyl optionally substituted by hydroxy, lower alkanoyloxy containing from 1 to 3 carbon atoms, halogen, trifluoromethyl or alkyl containing from 1 to 3 carbon atoms, aminoalkyl containing from 1 to 3 carbon atoms, or hydroxy alkyl containing from 1 to 3 carbon atoms, or amino protected in the forms of phthalimide or enamines derived from acetoacetates, acetylacetone, acetoacetamide or acetoacetonitrile, (ii) hydroxy or acyloxy containing from 1 to 7 carbon atoms, carbamoyloxy, or aralkyloxy containing from 7 to 12 carbon atoms, (iii) carboxy or alkoxycarbonyl containing from 2 to 7 carbon atoms, imdamyloxyecarbonyl, phenexyecarbonyl, or (iv) azide, cyame, carbamoyl, alkoxysulfonyl, sulfo, or alkoxysulfonyl;
(8) 2-sydnen-3-alkanoyl containing from 3 to 5 carbon atoms;
(9) (2- or 4-pyriden-1-yl)acetyl;
(10) 5-aminoadipoyl protected at the amino group by aroyl or alkenoyl containing from 1 to 10 carbon atoms, chloroalkanoyl containing from 1 to 5 carbon atoms or alkoxycarbonyl containing from 2 to 10 carbon atoms; or 5-aminoadipoyl protected at the carboxy group by benzhydryl, 2,2,2-trichloroethyl, trialkylsilyl, alkyl containing from 1 to 6 carbon atoms, nitrobenzyl or methoxybenzyl; and
(11) acryl groups of the formula:

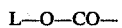

in which L is an easily removable optionally substituted hydrocarbon group containing from 1 to 8 carbon atoms (e.g. 2,2,2-trichloroethyl, isobornyl, tertiary butyl, 1-methylcyclohexyl, 2-alkoxy tertiary butyl, benzyl, p-nitrobenzyl or p-methoxybenzyl).

Alternatively, A and B considered together can represent a diacyl group derived from a polybasic carboxylic acid containing from 4 to 12 carbon atoms, alkylidene containing from 1 to 6 carbon atoms or arylmethylidene containing from 7 to 9 carbon atoms.

In the above, examples of Ar groups are furyl, thienyl, pyrryl, examelyl, isexazelyl, oxadiazelyl, oxatriazolyl, thiamelyl, isothiazelyl, thiadiazelyl, thiatriazolyl, pyrazelyl, imidamelyl, triamelyl, tetrazelyl, phenyl, pyridyl, pyrimidyl, pyramimyl, pyridesimyl, triazinyl and dihydrophenyl, each being optionally substituted to halogen, alkyl containing from 1 to 3 carbon atoms, hydroxy, aminomethyl or alkoxy containing from 1 to 3 carbon atoms.

The carboxy protecting group which is represented by X can contain up to 20 carbon atoms and can be an oxygen function such as, for example, alkoxy containing from 1 to 8 carbon atoms (e.g., methoxy, ethoxy or tertiary butoxy), aralkoxy containing from 7 to 20 carbon atoms (e.g. benzyloxy, methoxybenzyloxy, nitrobenzyloxy, diphenylmethoxy or trityloxy), mono- or bi-cyclic aryloxy (e.g. phenoxy or naphthyloxy), or organo metaloxy (e.g. trimethylstannic oxy or trimethylsilyloxy), organic or inorganic acyloxy containing up to 8 carbon atoms, or metal oxy of groups I, II or III in the periodical table (e.g. sodicoxy, potassicoxy, or magnesiodioxy); or X may be selected from sulfur functions such as those forming thiol ester, thiocarboxy or like groups; nitrogen functions such as those forming amides hydrazides, azide or like groups; or X may be selected from other carboxy-protecting groups.

These groups can, where possible, be interrupted by a hetero atom in the nucleus, unsaturated, or substituted by a substituent such as those referred to above (e.g. the nitrogen, oxygen, sulfur, carbon or phosphorous functions referred to above or halogen). Among preferable carboxy protecting groups X are those forming haloalkyl esters containing from 1 to 5 carbon atoms, acylalkyl esters containing from 2 to 10 carbon atoms, alkoxyalkyl- or aminoalkyl esters containing from 2 to 8 carbon atoms, arylester or aralkyl esters containing from 7 to 20 carbon atoms, esters with an oxime containing from 2 to 10 carbon atoms, N-alkoxyamide containing from 1 to 5 carbon atoms, imide with saccharin, imide with phthalimide, N,N'-diisobutylhydrazide, metal salts, or alkylamine salts containing from 1 to 6 carbon atoms, or groups equivalent in effect to these groups (in the above, specified numbers of carbon atoms are for groups X).

Antibacterially preferred carboxy-protecting groups X include those which form acyloxymethyl esters, phenacyl esters, the benzaldexime ester, the N,N-dimethylaminomethyl ester, alkali metal salts, alkaline earth metal salts, acylated alkaline earth metal salts, and ether groups equivalent in effect to these groups. Preferred carboxy protecting groups X include tert butoxy benzyloxy, benzhydryloxy, p-nitrobenzyloxy, p-methoxybenzyloxy, 2,2,2-trichloroethoxy and alkali metal-oxy.

Halogen which may be represented by Hal in the formulae can be a chlorine, bromine, iodine, or fluorine, in which chlorine and bromine are most preferable.

The thiol substituent R can be that easily removable without adverse effect on the other part of the molecule prior to or during cyclization reaction. It can be an acyl group, e.g. tertiary butoxycarbonyl, carbobenzoxy, cycloproplmethoxycarbomyl, cyclopropylethoxycarbonyl, 2,2,2-trichloroethoxycarbonyl, 2-methanesulfonylethoxycarbonyl) 1-alkoxy or acyloxyalkyl group containing 2 to 10 carbon atoms (e.g. methoxymethyl, ethoxymethyl, acetoxymethyl, 1-benzoylexyethyl), mono- or dicyclic aromatic thio group (e.g. thiadiazolylthio, thiazolylthio, benzothiazolylthio, phenylthio, e-nitrophenylthio, naphthylthio); and like groups.

As stated above, A, B, and R can be combined to form an azetidinothiazoline ring system represented by following formula:

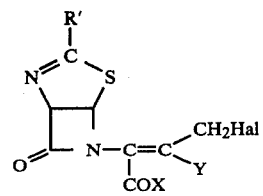

wherein R' is a group of an acyl represented by R'CO—; Nal, X and Y are as defined above, which can easily be hydrolyzed with an aqueous acid to give 4-mercapto-3-R'CONH-azetidinone compounds.

The enamine derivatives of the compound (I) are the compounds (I) where the hydroxyl group is substituted by an amine group containing from 2 to 20 carbon atoms. Preferable amino group include dialkylamino, alkylaralkylamino, alkylalkenylamino, alkyleneamine, diaralkylamino, dialkenylamino, and like amine groups optionally substituted by an inert group, the main nucleus of which can be interrrupted by a hetero atom. The groups are of intermediate character, and it is removed from the product in the final step. Therefore, the type of the group can be varied considerably, so far as the object of the reactions is not disturbed by the variation. Most preferable groups are morpholino, alkylenamino containing 4 to 8 carbon atoms, dialkylamino containing 2 to 6 carbon atoms, diaralkylamino containing 14 to 20 carbon atoms, optionally substituted by an inert group e.g. alkyl or halogen. The enamino group has advantage over other various substituents in that it facilitates desired halogenation, and that it is hydrolyzed under most mild condition, as is explained later.

More preferable compounds (I) provided by this invention are represented by following formulae

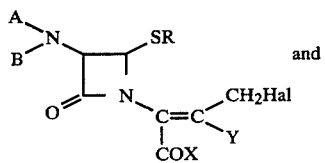 and

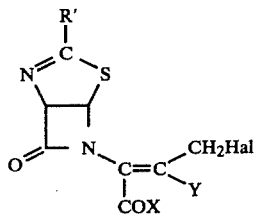

wherein A is a phenylacetyl or phenoxyacetyl; B is a hydrogen; R is a hydrogen, methoxymethyl, carbobenzoxy, cyclopropylmethoxycarbonyl, or benzothiazol-2-ylthio; Hal is a chlorine or bromine; X is a methyl, benzyl, p-nitrobenzyl, benzhydryl, or 2,2,2-trichloroethyl; Y is a piperidine, morpholine, dimethylamine, or hydroxy; and R' is a benzyl or phenoxymethyl, and when Y is a hydroxy, it can be in an oxo form.

Another class of compounds provided by this invention is represented by the following formula

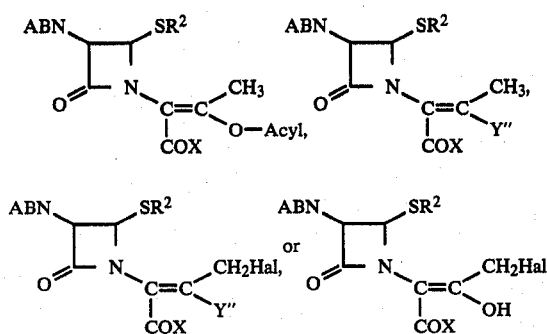

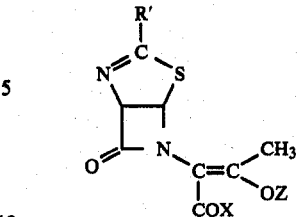

wherein ABN is an amine or substituted amine containing up to 20 carbon atoms; $R^2$ is a hydrogen or thiol substituent containing up to 20 carbon atoms; X is a hydrogen or thiol substituent containing up to 20 carbon atoms; X is a hydroxy or carboxy protecting group containing up to 20 carbon atoms; Acyl is a carbonic acyl group containing up to 20 carbon atoms; and Y" is a disubstituted amino containing 2 to 20 carbon atoms.

More preferable compounds are represented by the above formula in which ABN is a phenoxyacetamido, $R^2$ is a carbobenzoxy, cyclopropylmethoxycarbonyl, methoxymethyl, or benzethiazel-2-ylthio, X is a 2,2,2-trichloroethoxy or p-nitrobenzyloxy, Acyl is a cyclopropylmethoxycarbonyl, carbobonzoxy, methanesulfonyl, or toluene-p-sulfonyl, Y" is a morpholin-4-yl, or piperidin-1-yl, and Hal is a bromine; or in which ABN is a phthalimide, $R^2$ and Acyl each is a carbobenzoxy or cyclopropylmethoxycarbonyl, X is a methoxy, Y" is a piperidin-1-yl or morpholin-4-yl, and Hal is a bromine.

A mercaptoazetidine compound represented by following formula is also prepared easily by the deprotection method of this invention:

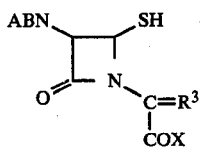

wherein ABN and X are as defined above; and $R^3$ is a hydrogen, isopropenyl, isopropylidene, or 1-hydroxyethylidene.

More preferable mercaptoazetidine compounds are represented by the above formula in which ABN is a phenoyacetamido, X is a p-nitrobenzyloxy, and $R^3$ is a isopropenyl, isopropylidene, or 1-hydroxyethylidene, or in which ABN is a phenoxyacetamido, X is a 2,2,2-trichloroethoxy, and $R^3$ is a 1-hyroxyethylidene; or in which ABN is a phenoxyacetamido, X is a tertiary butoxy, and $R^3$ is a hydrogen; or in which ABN is a phenylacetamide, X is a p-nitrobanzyloxy, and $R^3$ is a isopropenyl.

A sulfoxylated azetidine compound represented by following formula also is a useful starting material for the process provided by this invention:

wherein R' is a group of an acyl group R'CO—; X is as defined above; and Z is an aliphatic or aromatic sulfonyl containing up to 20 carbon atoms.

More preferable compounds are represented by the above formula in which R' is a phenoxymethyl, Z is a methanesulfonyl, and X is a p-nitrobenzyloxy, 2,2,2-trichloroethoxy, benzyloxy, or benzhydryloxy; or in which R' is a benzyl, Z is a methanesulfonyl, and X is a p-nitrobenzyloxy, 2,2,2-trichloroethoxy, benzyloxy, or benzhydryloxy; or in which R' is a phenoxymethyl; Z is a toluene-p-sulfonyl, and X is a p-nitrobenzyloxy, or 2,2,2-trichloroethoxy.

The sulfoxylated compounds can be treated by a secondary amine containing 2 to 20 carbon atoms to give enamine compounds provided by this invention and represented by following formula

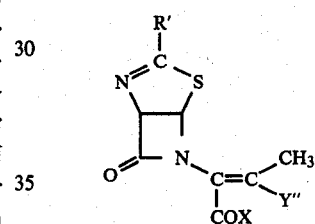

wherein R' and X are as defined above; and Y" is a disubstituted amino containing 2 to 20 carbon atoms.

More preferable enamine compounds are represented by the above formula in which R' is a phenoxymethyl, X is a p-nitrobenzyloxy, 2,2,2-trichloroethoxy, benzyloxy, or benzhydryloxy, and Y" is a morpholine; or in which R' is a benzyl, Y" is a morpholine, and X is a p-nitrobenzyloxy, 2,2,2-trichloroethoxy, benzyloxy, or benzyhydryloxy; or in which R' is a benzyl, Y" is a dimethylamine, and X is a p-nitrobenzyloxy; or in which R' is a benzyl, Y" is a piperidine, and X is a 2,2,2-trichloroethoxy.

The enamine compounds can be halogenated mildly to give haloenamine compounds provided by this invention, represented by following formula

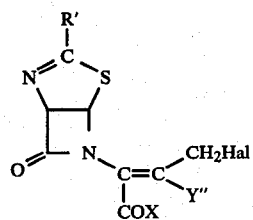

wherein R', X, and Y" are as defined above, and Hal is a halogen.

More preferable haloenamine compounds are represented by the above formula in which R' is a phenoxymethyl, Y" is a morpholine, Hal is a bromine, and X is a p-nitrobenzyloxy, 2,2,2-trichloroethoxy, benzyloxy, or benzhydryloxy; or in which R' is a benzyl, Y" is a morpholine, Hal is a bromine, and X is a p-nitrobenzyl, 2,2,2-trichloroethoxy, benzyloxy, or benzhydryloxy; or in which R' is a phenoxymethyl, Y" is a morpholine, Hal is a chlorine, and X is a p-nitrobenzyloxy; or in which R' is a benzyl, Y" is a dimethylamine, Hal is a bromine, and X is a p-nitrobenzyloxy; or in which R' is a benzyl, Y" is a piperidine, Hal is a bromine, and X is a 2,2,2-trichloroethoxy.

The haloenamine compounds are hydrolyzed mildly to give enel compounds represented by following formula, which also are compounds provided by this invention:

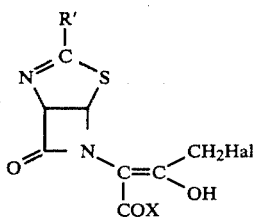

wherein R', X, and Hal are as defined above, or that in its exe form.

More preferable enel compounds are represented by above formula in which R' is a phenoxymethyl, Hal is a bromine, and X is a p-nitrobenzyloxy, 2,2,2-trichloroethoxy, benzyloxy, or benzhydryloxy, or in which R' is a phenoxymethyl, Hal is a bromine, and X is a p-nitrobenzyloxy, 2,2,2-trichloroethoxy, benzhydryloxy, or benzyloxy; or in which R' is a benzyl, Hal is a bromine, and X is a p-nitrobenzyloxy, 2,2,2-trichloroethoxy, benzyloxy, or benzhydryloxy; or in which R' is a phenoxymethyl, X is a p-nitrobenzyloxy, and Hal is a chlorine.

The haloenamine compounds can also be hydrolyzed to give mercaptoenamine compounds represented by following formula, which are also compounds provided by this invention.

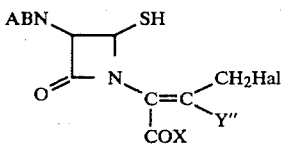

wherein ABN, X, Hal and Y" are as defined above.

More preferable mercaptoenamine compounds are represented by above formula in which ABN is a phenoxyacetamide, X is a p-nitrobenzylozy, 2,2,2-trichloroethoxy, benzyloxy, or benzhydryloxy, Y" is a morpholine or dimethylamine, and Hal is a bromine; or in which ABN is a phenylacetamide, X is a p-nitrobenzyloxy, 2,2,2-trichloroethoxy, benzyloxy, or benzhydryloxy, Y" is a morpholine or piperidine, and Hal is a bromine; or in which ABN is a phenoxyacetamide, X is a p-nitrobenzyloxy, Y" is a morpholine, and Hal is a chlorine.

The enel or mercapteenamine compounds can be hydrolyzed to give the last intermediates of the process, namely mercapteenel compounds represented by following formula, which also are a compounds provided by this invention.

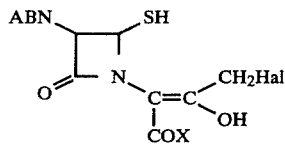

wherein ABN, X, and Hal are as defined above, or that in its oxo form.

More preferable mercaptoenol compounds are represented by above formula in which ABN is a phthalimido, X is a methoxy, and Hal is a bromine; or in which ABN is a phenoxyacetamido, Hal is a bromine, and X is a p-nitrobenzyloxy, 2,2,2-trichloroethoxy, benzyloxy, or diphenylmethoxy; or in which ABN is a phenylacetamido, Hal is a bromine, and X is a p-nitrobenzyloxy, 2,2,2-trichloroethoxy, benzyloxy, or benzhydryloxy, or in which ABN is a phenoxyacetamido, X is a p-nitrobenzyloxy, and Hal is a chlorine.

The starting materials (1) for the cyclization reactions, 4-substituted thio-3-(amino or substituted amino)-2-oxo-α-(1-ethylidene)azetidine-1-acetic acid or the derivatives at their carboxy group can be prepared from penicillin 1-oxide by reaction of phosphite esters, acetic anhydride, etc., giving α-isopropenylazetidine-1-acetic acid or its derivatives; which is oxidized with ozone to give the starting material where the α-substituent is 1-hydroxyethylidene or 1-acetyl; which in turn is treated with acylating reagents, aminating reagents, reactive nitrogen introducing reagents, etc., to give the corresponding starting materials. Further, the starting materials can also be prepared from an azetidine-2-one derivative and a reactive derivatives of acetoacetic acids.

The process (1) can be effected by treating the compound (1) with a halogenating reagent. The halogenating reagent includes that which halogenates through halogen cation or halogen radical or its equivalents. Representative halogenating reagents belong to the categories illustrated below:

1. $X'_2$ $X'_2$, BrCl, IBr, $C_6H_5I.X'_2$, $C_5H_5N.HX'.X'_2$, $C_6H_5N(CH_3)_2X'.X'_2$, $(alkyl)_2SO_4. HX'$, $CuX'_2$.

2. —OX'

$(alkyl)OX'$, $HOX'$, $(acyl)OX'$.

3. =NX'

$(alkyl)_4NX',X'_2$, $NO_2X'$, $(acyl)NHX'$, $(Acyl)_2NX'$.

4. —SX'

$SX'_2$, $S+X_2$.

5. ≤CX'

$X'_2CHOCH_3$, $CX'_4$, α-haloketones, α-halosulfone, or like reagents.

where alkyl and acyl contain up to 7 carbon atoms; and X' is a chlorine, bromine or iodine.

When these halogenating reagents are used as those through halogen radicals, the reaction is carried out by mediation with heat, light, peroxide (peracid, peroxide, hydroperoxide, etc.), azo compound (azobisisobutyronitrile, etc.), or other radical initiator.

When these halogenating reagents are used as those through halogen cation, the reaction is carried out, if required, in the presence of an acid trapping reagent (organic or inorganic base e.g. sodium carbonate, pyridine, quinoline, lutidine, diethylamine, triethylamine, etc.). The onium ion forming starting compounds (1) are more easily halogenated to give the objective compounds in higher yield under mild condition.

When these halogenating reagents are used through carbanion of the starting material (1), the starting materials (1) are treated with an anion forming reagent (alkali metal hydrides, alkali metal amides, alkali metal alkoxide, lithium dialkylamine, hexaalkyldisilazane lithium, trialkylamine, Grignard reagents etc.) to form carbanion, followed by the action of a halogenating reagent. The reaction is preferably carried out in an aprotic solvent at lower temperature, so as to avoid side reactions.

The reaction of the starting materials with the halogenating reagents is preferably carried out in an inert solvent.

The solvents include a hydrocarbon (pentane, hexane, benzene, toluene, etc.), halogenated hydrocarbon (methylene chloride, chloroform, carbon tetrachloride, dichlorobenzene, etc.), ester (ethyl acetate, butyl acetate, methyl benzoate, etc.), ketone (acetone, cyclohexanone, benzophenone, etc.), ether (diethyl ether, ethyleneglycol dimethyl ether, tetrahydrofuran, tetrahydropyran, dioxane, morpholine, anisole, etc.), alcohol (methanol, ethanol, ethyleneglycol, benzylalcohol, etc.), carboxylic acid (acetic acid, propionic acid, etc.), base (butylamine, triethylamine, pyridine, picoline, etc.), amide (dimethylformamide, dimethylacetamide, hexamethylphosphorotriamide, etc.), nitrile (acetonitrile, benzonitrile, etc.), nitrohydrocarbon, sulfoxide (dimethyl sulfoxide, etc.), water, liquid ammonia solvents, and other solvents and their mixtures.

Especially preferable solvents are aromatic hydrocarbon, hlogenated hydrocarbon, ester, ether, amide, and acid, solvents.

The cis-trans isomerization possibly occurs during the reaction at the substituent on position α of the geometric isomer, which reaction is included in the scope of this invention.

Halogenation of compounds representable by the formula (1) provided Y is other than amino took place smoothly in some cases and with difficulty in other cases. Main difficulty were the position where the halogen atoms was introduced. In other words, the priority of the desired position to other position in the molecule for halogenation was rather small, and it differs from one compound to another. Another factor which restricts Y to the scope given above is found not in the halogenation but in the following reactions, i.e. (i) ease of deprotection to give a compound (I) where Y is hydroxy; and (ii) ability to cyclize giving the desired cephem compound (4). The compounds representable by formula (1) provided Y is other than hydroxy cyclized unefficiently or insignificantly. From these observations, Y is resticted to include a hydroxy and substituted amino, as is explained above.

The deprotection (2) of the compound (2) can be carried out by treating the compound (2) with aqueous acid for the thiazolinoazetidine compound, and by treating the compound (2) where R is a carbonic acyl, with a Lewis acid.

The decomposition of the azetidinothiazoline compound with an aqueous acid is a new generic reaction for obtaining the 4-mercapto-3-carboxylic acylamino-2-oxoazetidine derivatives according to the reaction scheme

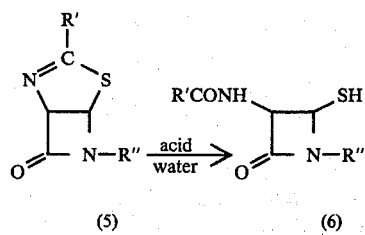

wherein R' is a group of an acyl group R'CO; R'' is a hydrogen or hydrocarbon group (e.g. alkyl, alkenyl, aralkyl, aryl), acyl derived from organic or inorganic acid, silyl, sulfenyl, or other monovalent amino protecting group, optionally substituted by a halogen, sulfur, oxygen, nitrogen, carbon, or phosphorous functions referred to above.

It can be carried out by treating a thiazolinoazetidine (5) with an acid and water. The reaction of water is necessary for cleavage of thiazoline ring to give 4-mercapto and 3-acylamine of azetidine ring. The preferable acids include mineral acid (e.g. hydrogen halide, sulfuric acid, nitric acid, phosphoric, acid, perchloric acid, chloric acid), sulfonic acid (e.g. alkanesulfonic acid, arylsulfonic acid, aralkylsulfonic acid, especially α-haloalkanesulfonic acid), α-halocarboxylic acid, polycarboxylic acid, preferably acids having dissociation constants of at least 0.01. More specific acids include strong acids e.g. perchloric acid, trifluoroacetic acid, trichloroacetic acid, dichloroacetic acid, trifluoromethanesulfonic acid, trichloromethanesulfonic acid, hydrogen borofluoride, hydrochloric acid, hydrogen fluoride, hydrobromic acid, nitric acid, phosphoric acid, benzenesulfonic acid, toluenesulfonic acid, bromobenzenesulfonic acid, methanesulfonic acid, ethanesulfonic acid, etc.

The said reaction can be carried out in a solvent referred to above.

More preferable solvents are polar solvents capable of dissolving water and acid (e.g. ether, ketone, alcohol, amide, sulfoxide, water), the solvents capable of dissolving the starting material (5) (e.g. halohydrocarbon, ester, ether, ketone), and the mixtures thereof.

When a strong acid is used, side reaction e.g. decomposition of the azetidinone ring, can take place. The yield can be improved by selection of reaction conditions e.g. concentration, temperature, reaction time, etc. Generally, the reaction proceeds even at room temperature rapidly, sometimes within 10 minutes to 1 hour, to give the objective compound in high yield.

The products are unstable to alkali and oxidation. Therefore, reactions and working up should be done without exposure to such conditions.

Further, the preparation of the mercapto compound (8) by eliminating the thiel substituent R being carbonic acyl can be carried out by treating the compound (7) with a Lewis acid according to the reaction scheme

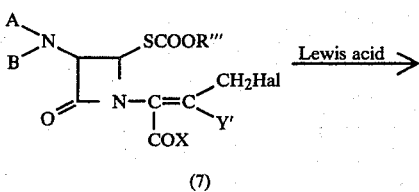

-continued

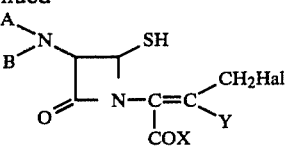

wherein A, B, X, Y', and Hal are as defined above; and R''' is a hydrocarbyl containing 1 to 20 carbon atoms optionally substituted by an inert group e.g. halogen aralkyl, nitro, alkoxy or alkyl containing 1 to 5 carbon atoms, or carbalkoxy. The carbonic acyl can be carbobenzoxy, tertiary butoxycarbonyl, cyclopropylmethoxycarbonyl, 2,2,2-trichloroethoxycarbonyl, methanesulfonylethoxycarbonyl, isobornyloxycarbonyl), and the Lewis acid can be boron trihalide, aluminum halide, titanium dihalide, titanium tetraakanoate, and like Lewis acids. The reaction can be carried out mildly in high yield.

The cyclization (3) can be effected by treating the compound (3) with an
(i) acid,
(ii) base, or
(iii) solvent, if required in the presence of catalyzer. or under any condition which cyclizes the starting material to give 3-cephem nucleus. The starting compounds seemed to have tendency to cyclize nearly automatically, and under various weak conditions, the object cephem compounds can be isolated in good yield. The mercapto group at position 4 of the starting materials can be in the form of mercaptide anion. It is unnecessary to use the isolated starting material (3) for the reaction, and every method which yields the starting material (I) where R is a hydrogen can be used for the reaction. Typical examples of the method are treatment of α-[3-(phenoxymethyl or benzyl)-7-oxo-2,6-diaza-4-thiabicyclo[3,2,0]hept-2-en-6-yl]-α-(2-haloacetyl)acetic acid, α-[4-mercapto-3-(phenoxyacetyl or phenylacetyl)amino-2-oxoazetidin-1-yl]-α-(2-haloacetyl)acetic acid, or their derivatives at the carboxy or their enamine derivatives at the α-(2-haloacetyl) group, under aqueous acid condition. The treatment is consistent with the condition for cyclization cited above (i), and the obtained product is the objective cephem compound (4).

The acids used to acidify the reaction medium include a mineral acid (e.g. hydrochloric acid, hydrobromic acid, sulfuric acid, nitric acid, phosphoric acid, perchloric acid, sulfurous acid), sulfonic acid (e.g. alkanesulfonic acid, arylsulfonic acid), phosphonic acid, carboxylic acid (e.g. formic acid, acetic acid, haloalkanoic acid, oxalic acid, phthalic acid), and other organic or inorganic acid, or their salts with a weak base (e.g. aromatic or aliphatic base, ammonia, alkaline earth metal, aluminum, silver), or acidic salts of the said acid with common base including an alkali metal salts. Lewis acids can also be used favourably in an aprotic solvent.

The bases used to make the medium basic include preferably the said weak base. Strong bases (e.g. alkali metal hydroxide, alkali metal carbonate, tertiary ammonium hydroxide), can be used under selected mild condition because they decompose the starting or produced compounds, especially the β-lactam moiety. Le s base can also be used.

The catalyst for cyclization can be a neutral or basic silica gel, alumina, diatomaceous earth, florisil, and other catalysts.

In some cases, cyclization takes place by the action of solvent (e.g. solvent of higher polarity including amides (hexamethylphosphorotriamide, dimethylformamide, formamide, etc.) alcohol, water.) alone. In the cases, polar solvents accelerates the reaction. It can be assumed the reaction is a result of catalysis with hydrogen halide produced by the initial reaction.

The reaction is preferably carried out in a solvent referred to above under heating or cooling, or at room temperature. If required, the reaction medium is stirred under inert gas.

Preferable solvents are polar solvent e.g. alcohol, carboxylic acid, amide, nitile, nitrohydrocarbon, sulfoxide, water solvents, and a solvents highly capable of solubilizing the starting materials, e.g. ester, ether, halohydrocarbon solvents which sometimes facilitates the reaction. The reaction generally proceeds quickly at room temperature to give the objective cephem or cephem compounds in high yield.

The reaction products (2)-(4) can be isolated from the reaction mixture by conventional methods e.g. removing unreacted material, by-product, solvent, or the like, and be purified by conventional method e.g. recrystallization, chromatography, reprecipitation.

The final products are 3-hydroxy-3-cephem-4-carboxylic acid or 3-oxocephem-4-carboxylic acid (4). In some instances, the substituents at position 3 or 7 on the cephem ring change during the reaction or working up, and as a result, the corresponding substituents in the starting and produced materials differ each other. If desired, such substituents can be recovered or transformed into other required one by conventional methods. Such cases are also included in the scope of the present invention.

In the cephem nucleus of the products, there is a double bond linked to carbon atoms at position 3. The double bond can be directed to position 2,4, or the 3-substituent oxygen, or their mixture, according to the condition of reaction, working up, etc. These cases are also included in the scope of this invention, but usually, the main product has exclusively in 3-cephem or 3-oxo double bond isomer.

During the cyclization, it is certain to form intermediary compounds (3) regardless of whether isolation has been carried out or not.

The halogenation (1), deprotection (2). and cyclization (3) can be carried out in one pot, namely without isolating intermediates, and even without removing each reaction solvents. Therefore, the reactions practically be done as simply as one step reaction (see Examples 2(2) and (3), and Examples 9 to 17 of Part III Cyclization).

Some of the starting materials are (prepared by the following procedures.

Preparation 1

To a solution of methyl α-[4-mercapto-3-phthalimido-2-oxoazetidin-1-yl]-α-(1-hydroxyethylidene)acetate (100 mg) in tetrahydrofuran (3 ml) is added benzyl chloroformate (100 mg), and the mixture is cooled to −65° C. To the solution is added triethylamine (60 mg) and stirred for 1 hour. After warming to room temperature, the mixture is evaporated. Purification of the residue by chromatography over silica gel gives methyl α-[4-benzyloxycarbonylthio-3- phthalimido-2-oxoazetidin-1-yl]-α-(1-benzyloxycarbonylethylidene)acetate (160 mg). Yield: 94%. The product contains no isomer at position α, IR: $\nu_{max}^{CHCl_3}$ 1790, 1780, 1730 cm$^{-1}$. NMR: $\delta^{CDCl_3}$ 8.00∝7.50m4H, 7.40s5H, 7.30s5H, 6.27d(5 Hz)1H, 5.90d(5 Hz)1H, 5.27s2H, 5.17s2H, 3.70s3H, 2.47s3H.

Preparaton 2

To a solution of methyl α-(4-mercapto-3-phthalimido-2-oxoazetidin-1-yl)-α-(1-hydroxyethylidene)acetate (50 mg) in tetrahydrofuran (2 ml) is added cyclopropylmethyl chloroformate (50 mg), and the mixture is cooled to −65° C., followed by the addition of triethylamine (30 mg) in tetrahydrofuran (0.5 ml). After stirring for 1 hour, the mixture is warmed slowly to room temperature, evaporated under reduced pressure, and purified by chromatography over silica gel using benzene containing 5% ether to give methyl α-[4-cyclopropylmethoxycarbonylthio-3-phthalimido-2-oxoazetidin-1-yl]-α-(1-cyclopropylmethoxycarbonyloxyethylidene)acetate (61 mg). Yield: 79%.

The product is a mixture of the geometric isomers of the substituent at position α (ca. 3:2). IR: $\nu_{max}^{CHCl_3}$ 1790, 1780, 1730 om$^{-1}$. NMR: $\delta^{CDCl_3}$ 8.00–7.60m4H, 6.18d(5 Hz)3/5H, 6.10d(5 Hz)2/5H, 5.85d(5 Hz)3/5H, 5.78d(5 Hz)2/5H, 4.30–3.80m4H, 3.87s6/5H, 3.82s9/5H, 2.53s6/5H, 2.47s9/5H, 1.60–0.90m2H, 0.900.10m8H.

Preparation 3

To a solution of 2,2,2-trichloroethyl α-[4-(2-benzothiazolyl)dithio-3-phenoxyacetamido-2-oxoazetidin-1-yl]-α-(1-hydroxyethylidene)acetate in tetrahydrofuran are added an acid chloride and triethylamine, and the mixture is let react for 1 to 3 hours, and is worked up by conventional method to give following esters:

(1) 2,2,2-trichloroethyl α-[4-(2-benzothiazolyl)dithio-3-phenoxyacetamido-2-oxoazetidin-1-yl]-α-(1-methanesulfonyloxyetylidene)acetate, IR: $\nu_{max}^{CHCl_3}$ 3440, 1795, 1753, 1698, 1640, 1602 cm$^{-1}$. NMR: $\delta^{CDCl_3}$ 2.70s3H, 3.38s3H, 4.6m4H, 5.25d(5 Hz)1H, 5.78d(5 Hz)1H, 6.8–8.0m10H;

(2) 2,2,2-trichloroethyl α-[4-(2-benzothiaxolyl)dithio-3-phenoxyacetamido-2-oxoazetidin-1-yl]-α-(1-toluene-p-sulfonyloxyethylidene)acetate, IR: $\nu_{max}^{CHCl_3}$ 3420, 1780, 1770, 1685 cm$^{-1}$. NMR: $\nu^{CDCl_3}$ 2.28s3H, 2.50s3H, 4.55s2H, 4.63ABq(12 Hz)2H, 5.08dd(7;5 Hz)1H, 5.78d(5 Hz)1H, 6.65–8.22m14H;

(3) p-nitrobenzyl α-[4-(2-benzothiazolyl)dithio-3-phenoxyacetamido-2-oxoazetidin-1-yl]-α-(1-cyclopropylmethoxycarbonylethylidene)acetate, IR: $\nu_{max}^{CHCl_3}$ 3420, 1780, 1685, 1640 cm$^{-1}$. NMR: $\delta^{CDCl_3}$ 0.05–1.52m5H, 2.47s3H, 3.95+4.02d(2H), 4.50+4.58s2H, 4.80–5.40m4H, 6.67–8.13m14H.

(4) 2,2,2-trichloroethyl α-[4-(2-benzothiazolyl)dithio-3-phenoxyacetamido-2-oxoazetidin-1-yl]-α-(1-cyclopropylmethoxycarboxyethylidene)acetate, IR: $\nu_{max}^{CHCl_3}$ 3450, 1790, 1690, 1650 cm$^{-1}$. NMR: $\delta^{CDCl_3}$ 0.13–1.55m5H, 2.52s3H, 4.10d(7 Hz)2H, 4.53ABq(12 Hz)2H, 4.63s2H, 5.11dd(5 Hz)1H, d(7;5 Hz)1H, 5.75d(5 Hz)1H, 6.72–8.07ml10H.

Preparation 4

To a solution of p-nitrobenzyl α-[4-cyclopropylmethoxycarbonylthio-3-phenoxyacetamido-2-oxoazetidin-1-yl]-α-(1-hydroxyethylidene)acetate (904 mg) in a mixture (9.5 ml) of tetrahydrofuran and hexamethylphosphorotriamide (20:1) are added methanesulfonyl chloride (0.26 ml) and triethylamine (0.37 ml). After 2 hours, the reaction mixture is poured into ice water, and extracted with chloroform. The extract solution is washed with water, dried, and evaporated to give p-nitrobenzyl α-[4-cyclopropylmethoxycarbonylthio-3-phenoxyacetamido-2-oxoazetidin-1-yl]-α-(1-methanesulfonyloxyethylidene)acetate (1.12 g). Yellow foam. IR: $\nu_{max}^{CHCl_3}$ 3426, 1785, 1722–1704br, 1640, 1601, 1160, 1175, 986 cm$^{-1}$. NMR: $\delta^{CDCl_3}$ 0.32–1.25m5H, 2.57s3H, 2.72s3H, 3.99d(7 Hz)2H, 4.55s2H, 5.33–5.99m4H, 6.82–7.62m7H 8.21d(8.5 Hz)2H.

According to similar acylation, following compounds are prepared.

(1) p-nitrobenzyl α-[4-cyclopropylmethoxycarbonylthio-3-phenoxyacetamido-2-oxoazetidin-1-yl]-α-(1-methoxycarbonyloxyethylidene)acetate, IR: $\nu_{max}^{CHCl_3}$ 1780, 1731, 1643, 1612, 1601 cm$^{-1}$. NMR: $\delta^{CDCl_3}$ 0.2–1.33m5H, 2.34s3/2H, 2.50s3/2H, 3.74s3/2H, 3.83s3/2H, 3,97d(7 Hz)2H, 4.52s2H, 5.26s2H, 5.53–6.00m2H, 6.79–8.24m9H.

(3) 2,2,2-trichloroethyl α-[4-(o-nitrophenyl)dithio-3-phenoxyacetamido-2-oxoazetidin-1-yl]-α-(1-cyclopropylmethoxycarbonyloxyethylidene)acetate, IR: $\nu_{max}^{CHCl_3}$ 3430, 1781, 1750sh, 1685, 1640 cm$^{-1}$. NMR: $\delta^{CDCl_3}$ 0.2–1.4m5H, 2.50s3H, 4.13d(8 Hz)2H, 4.53ABq(12Hz)2H, 4.56s2H, 5.15dd(5;8 Hz)1H, 5.43d(5 Hz)1H, 6.8–8.4m10H.

Preparation 5

To a solution of silver salt of 2,2,2-trichloroethyl α-[4-mercapto-3-phenoxyacetamido-2-oxoazetidin-1-yl]-α-(1-hydroxyethylidene)acetate (695 mg) in hexamethyl phoshorotriamide (8 ml) is added a mixture of cyclopropylmethyl chloroformate (480 mg) and triethylamine (180 mg), and the mixture is stirred for 1 hour. The reaction mixture is poured into ice water, and is extracted with benzene. The extract solution is washed with water, dried, and evaporated in leave residue. Purification of the residue by chromatography over silica gel to give 2,2,2-trichloroethyl α-[4-cyclopropylmethoxycarbonylthio-3-phenoxyacetamido-2-oxoazetidin-1-yl]-α-(1-cyclopropylmethoxycarbonyloxyethylidene)acetate (650 mg). Yield: 64.4%.

The product is a mixture (ca. 4:3) of the geometric isomers of the substituent at position α.

IR: $\nu_{max}^{CHCl_3}$ 3440, 1785, 1720 cm$^{-1}$. NMR: $\delta^{CDCl_3}$ 0.1–1.3m10H, 2.4s3H, 4.0m3H, 4.60s2H, 4.83s2H, 5.2–6.1m2H, 6.8–7.5m6H.

Preparation 6

To a solution of p-nitrobenzyl α-[4-cyclopropylmethoxycarbonylthio-3-phenoxyacetamido-2-oxoazetidin-1-yl]-α-(1-methanesulfonyloxyethylidene)acetate (1.12 g) in benzene (11 ml) is added morpholine (0.26 ml) under ice cooling, and the mixture is kept at 10° C. overnight. The reaction mixture is washed with water, dried, and evaporated under reduced pressure. Purification of the obtained residue (1 g) by chromatography over silica gel (10 g) using a mixture of benzene and ethyl acetate (1:2) gives p-nitrobenzyl α-[4-cyclopropylmethoxycarbonylthio-3-phenoxyacetamido-2-oxoazetidin-1-yl]-α-(1-morpholinoethylidene)acetate (602 mg). Foam.

IR: $\nu_{max}^{CHCl_3}$ 3430, 1774, 1694br, 1604, 1150 cm$^{-1}$. NMR: $\delta^{CDCl_3}$ 0.22m5H, 2.27+2.40s3H, 3.43m4H, 3.77m4H, 4.02d(6.4 Hz)2H, 4.57s2H, 5.05–5.27m3H, 5.89d(5.4 Hz)1H, 4.12–7.65m7H, 8.23d(8.4 Hz)2H.

According to the method similar to that described above, following compounds are prepared from the corresponding methanesulfonates:

(1) 2,2,2-trichloroethyl α-[4-(benzothiazolyl)dithio-3-phenoxyacetamido-2-oxoazotidin-1-yl]-α-(1-piperidinoethylidene)acetate, IR: $\nu_{max}^{CHCl_3}$ 3440, 1773, 1690, 1600 cm$^{-1}$. NMR: $\delta^{CDCl_3}$ 1.68brs6H, 2.4brs3H, 3.36brs4H, 4.63m4H, 5.0–5.7m2H, 6.8–8.0m10.

(2) p-nitrobenzyl α-[4-(2-benzothiazolyl)dithio-3-phenoxyacetamido-2-oxoazetidin-1-yl]-α-(1-piperidinoethylidene)acetate, NMR: $\delta^{CDCl_3}$ 1.63brs6H, 2.33brs3H, 3.3brs4H, 4.53s2H, 5.0–5.5m4H, 6.8–8.2ml4H.

Similarly, the following compounds are prepared from the corresponding chlorides:

(1) 2,2,2-trichloroethyl α-[4-cyclopropylmethoxycarbonylthio-3-phenoxyacetamido-2-oxoazetidin-1-yl]-α-(1-piperidinoethylidene)acetate, IR: $\nu_{max}^{CHCl_3}$ 3440, 1780, 1710, 1695 cm$^{-1}$. NMR: 0.2–1.3 m5H, 1.67brs6H, 2.40 or 2.27s3H, 3.35brs4H, 3.98d(7 Hz)1H, 4.57s2H, 4.73s2H, 5.13–6.07m2H., for the isomers.

(2) 2,2,2-trichloroethyl α-[4-(benzothiazolyl)dithio-3-phenoxyacetamido-2-oxoazetidin-1-yl]-α-(1-piperidinoethylidene)acetate cited above.

PREPARATION 7

To a solution of p-nitrobenzyl α-[3-phenoxymethyl-7-oxo-4-tris-2,6-diasobicyclo[3,2,0]hept-2-en-6-yl]-α-(1-hydroxyethylidene)acetate (504 mg) in tetrahydrofuran (8 ml) are added dropwise methanesulfonyl chloride (0.13 ml) and triethylamine (0.23 ml) under ice cooling. After 3 hours, the mixture is evaporated to leave residue, which is dissolved in methylene chloride, washed with water, dried over magnesium sulfate, and evaporated. Purification of the residue by chromatography over silica gel containing 10% water (15 g) using a mixture of benzene and ethyl acetate (5:1) gives p-nitrobenzyl α-[3-phenoxymethyl-7-oxo-4-thio, 2,6-diazabicyclo[3,2,0]hept-2-en-α-yl]-α-(1-methanesulfonyloxyethylidene)acetate (353 mg). Colorless foam.

The product contains no geometric isomer at position s, IR: $\nu_{max}^{CHCl_3}$ 1780, 1730 cm$^{-1}$. NMR: $\delta^{CDCl_3}$ 2.60s3H, 3.18s3H, 4.58+4.88ABq(14 Hz)2H, 5.24s2H, 5.92+6.08ABq(5 Hz)2H, 6.73–8.20m9H.

PREPARATION 8

To a solution of p-nitrobenzyl α-[3-phenoxymethyl-7-oxo4-thia-2,6-diazabicyclo[3,2,0]hept-2-en-6-yl]-α-(1-hydroxyethylidene)acetate (940 mg) in dimethylformamide containing 10% tetrahydrofuran (5 ml) is added toluene-p-sulfonyl chloride (456 mg). After cooling to −70° C., the solution is mixed with triethylamine (0.3 ml). The reaction mixture is allowed to warm slowly up to room temperature, poured into water, and extracted with ethyl acetate. The extract solution is washed with water, dried, and evaporated. The obtained residue is chromatographed over silica gel containing 10% water using benzene containing 5% ethyl acetate to give p-nitrobenzyl α-[3-phenoxymethyl-7-oxo-4-thia-2,6-diazabicyclo[3,2,0]hept-2-en-6-yl]-α-(1-toluene-p-sulfonyloxyethylidene)acetate (644 mg). IR: $\nu_{max}^{CHCl_3}$ 1785, 1735 cm$^{-1}$. NMR: $\delta^{CDCl_3}$ 2.45s3H, 4.75+4.20ABq (14 Hz)2H, 5.15s2H, 5.77s2H, 8.30–6.60m13H.

PREPARATION 9

To a solution of p-nitrobenzyl α-[3-phenoxymethyl-7-oxo-4-thia-2,6-diazabicyclo[3,2,0]hept-2-en-6-yl]-α-(1-methanesulfonyl)ethylidene)acetate (298 mg) in benzene (3 ml) is added morpholine (0.095 ml) at 7° to 10° C. After 130 minutes, the reaction mixture is filtered to give filtrate, which is poured into iced water, and is extracted with methylene chloride. The extract solution is washed with water, dried over magnesium sulfate, and evaporated to give p-nitrobenzyl α-[3-phenoxymethyl-7-oxo-4-thia-2,6-diazabicyclo[3,2,0]hept-2-en-6-yl]-α-(1-morpholinoethylidene)-acetate (284 mg). Foam. Yield: 97.1%.

The product is a mixture (ca. 1:1) of the geometric isomers at the substituent on position α.

IR: $\nu_{max}^{CHCl_3}$ 1768, 1685, 1612, 1603 cm$^{-1}$. NMR: $\delta^{CDCl_3}$ 1.90s1H, 2.42s1H, 3.17–3.43m4H, 3.52–3.83m4H, 4.87s2H, 5.21s2H, 5.58–6.00m2H, 6.80–8.22m9H.

PREPARATION 10

To a solution of 2,2,2-trichloroethyl α-[3-phenoxymethyl-7-oxo-4-thia-2,6-diazabicyclo[3,2,0]hept-2-en-6-yl]-α-(1-methanesulfonyloxyethylidene)acetate (1.52 g) in benzene (30 ml) is added morpholine (0.48 ml) at beneath 10° C. After stirring for 1 hour, the mixture is washed with water, dried, and evaporated. Purification of the obtained residue by chromatography over silica gel gives 2,2,2-trichloroethyl α-[3-phenoxymethyl-7-oxo-4-thia-2,6-diazabicyclo[3,2,0]hept-2-en-6-yl]-α-(1-morpholinoethylidene)acetate (0.76 g). Yield: 50%.

The product is a mixture of isomers at substituent on position α.

NMR: $\delta^{CDCl_3}$ 1.88+2.42s3H, 3.1–3.9m8H, 4.73ABq(12 Hz)2H, 4.95s2H, 5.7–6.2m2H, 6.8–7.5m5H.

PREPARATION 11

To a stirred solution of p-nitrobenzyl α-[3-phenoxymethyl-7-oxo-4-thia-2,6-diazabicyclo[3,2,0]hept-2-en-6-yl]-α-(1-hydroxyethylidene)acetate (500 mg) in tetrahydrofuran (20 ml) are added dropwise methyl chloroformate (200 mg) and triethylamine (216 mg) under ice cooling. After 1 hour, the reaction mixture is poured into ice water, and is extracted with ethyl acetate. The extract solution is washed with water, dried, and evaporated to give p-nitrobenzyl, α-[3-phenoxymethyl-7-oxo-4-thia-2,6-diazabicyclo[3,2,0]hept-2-en-6-yl]-α-(1-methoxycarbonyloxyethylidene)-acetate (546 mg). Foam. Yield 97%.

The product is a mixture (ca. 2:1) of the geometric isomers at position α.

IR: $\nu_{max}^{CHCl_3}$ 1783, 1732, 1642, 1612, 1600 cm$^{-1}$. NMR: $\delta^{CDCl_3}$ 1.95s1H, 2.47s2H, 3.68s1H, 3.80s2H, 4.54+4.86ABq(14 Hz) 4/3H, 4.86s2/3H, 5.25s3H, 5.73–6.03m2H, 6.70–8.16m9H.

PREPARATION 12

To a solution of 2,2,2-trichloroethyl α-[3-benzyl-7-oxo-2,6-diaza-4-thiabicyclo[3,2,0]hept-2-en-6-yl]-α-(1-hydroxyethylidene)-acetate (450 mg) in methylene chloride (7 ml) are added methanesulfonyl chloride (0.093 ml) and triethylamine (0.48 ml) at −25° C., and the mixture is kept at the same temperature for 40 minutes. To the produced solution of 2,2,2-trichloroethyl α-[3-benzyl-7-oxo-4-thia-2,6-diazabicyclo[3,2,0]hept-2-en-6-yl]-α-(1-methanesulfonyloxyethylidene)acetate is added dropwise morpholine (0.112 ml), and the mixture is stirred for 1.3 hours. The reaction mixture is washed with water, dried, and evaporated to give residue which is purified by chromatography over silica gel containing 10% water to give 2,2,2-trichloroethyl α-[3-benzyl-7-oxo-4-thia-2,6-diazabicyclo[3,2,0]hept-2-en-6-yl]α-(1-morpholinoethylidene)acetate (205 mg).

The product is a mixture (ca. 1:1.6) of the geometric isomers at position α.

MNR: $\delta^{CDCl_3}$ 1.67s+2.35s[3H], 2.83–4.00m8H, 2.31s2H, 4.45+4.88q (12 Hz):4.47+4.83q(12 Hz)[2H], 5.60–6.12m2H, 7.22s+7.23s[5H].

PREPARATION 13

To a solution of p-nitrobenzyl α-[3-benzyl-7-oxo-4-thia-2,6-diazabicyclo[3,2,0]hept-2-en-6-yl]-α-(1-methanesulfonyloxyethylidene)acetate (609 mg) in methylene chloride (3 ml) is added morpholine (0.2 ml) at −15° C., and the mixture is stirred for 50 minutes at the same temperature. The reaction mixture is poured into ice water, and is extracted with methylene chloride. The extract solution is washed with water, dried, and evaporated. Purification of the obtained foam (569 mg) by chromatography over silica gel (25 g) gives from the fractions eluted with a mixture of benzene and ethyl acetate (2:1) p-nitrobenzyl α-[3-benzyl-7-oxo-4-thia-2,6-diazabicyclo[3,2,0]hept-2-en-6-yl]-α-(1-morpholinoethylidene)acetate (452 mg). Yield: 75.5%, Foam.

The product contains no geomtric isomers at position α.

IR: $\nu_{max}^{CHCl_3}$ 1778, 1695, 1615 cm$^{-1}$. NMR: $\delta^{CDCl_3}$ 2.37s3H, 3.00–3.73m8H, 3.86s2H, 5.20s3H, 5.73+5.88ABq(3 Hz)2H, 7.15–8.28m9H.

These products are also novel and representable by the following formulae:

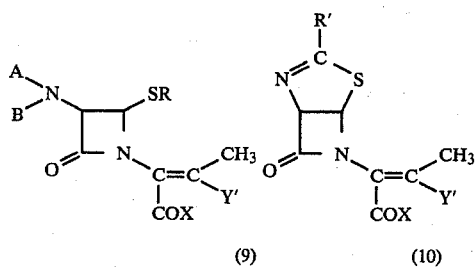

(9)　　(10)

wherein R, B, R, R', and X are as defined above; Y' is a carbonic acyloxy containing up to 12 carbon atoms, disubstituted amino containing 2 to 20 carbon atoms, or aromatic or aliphatic sulfonyl containing 1 to 20 carbon atoms.

Preferable groups for ABN- are phthalimido, phenoxyacetamido, and phenylacetamido; for X are a methyl, benzyl, p-nitrobenzyl, benzhydryl, and 2,2,2-trichloroethyl; for R are tertiary butoxycarbonyl, cyclopropylmethoxycarbonyl, carbobenzoxy, methoxymethyl, o-nitrophenylthio, and benzothiazol-2-ylthio; for Y' are cyclopropylmethoxycarboxy, carbobenzoxy, methoxycarboxy, alkyleneamino containing from 4 to 8 carbon atoms, morpholin-4-yl, dialkylamino containing from 2 to 6 carbon atoms, alkanesulfonyloxy containing from 1 to 12 carbon atoms, or arylsulfonyloxy containing from 4 to 20 carbon atoms; and for R' are benzyl and phenoxymethyl.

The compound (9) or (10) where Y is disubstituted amino can be prepared by following reactions in conventional procedures, as shown in Preparations cited above:

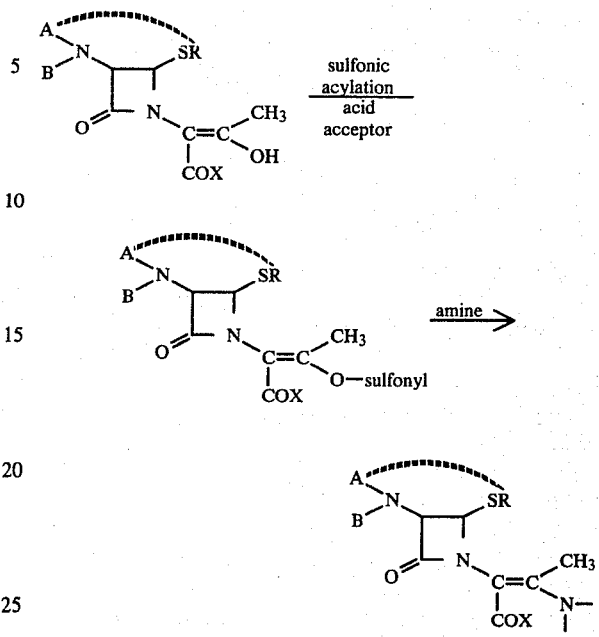

wherein A, B, R, X, and broken line are as defined above, at about −30° C. to 0° C.

The process can be carried out in one pot, namely it is unnecessary to isolate intermediates and to remove reaction solvents for any step to give the enamine compound.

The preparation of enamines by above process and halogenation (1), deprotection of thiol (2), and cyclization (3) can also be carried out in one pot, namely without isolating any intermediate, or even removing any solvent during reaction, giving up to 80% or more of the cephem compound (4) from the compound (9) or (10) where Y is a hydroxy. In other words, the reaction can be carried out as simply as one reaction. In this case the solvent is selected from that suitable for all reactions. Typical examples are ether solvents (e.g. tetrahydrofuran, tetrahydropyran, and dioxan), amide solvents (e.g. dimethylformamide, dimethylacetamide, and hexamethylphosphorotriamide), and halohydrocarbon solvents (e.g. chloroform, methylene chloride, and dichloroethane).

As stated above, this invention provides the higher yielding and simpler process from less expensive penicillins to give valuable key intermediates, the 3-hydroxy-3-cephem compounds.

Another aspect of this invention is oxidative cleavage of unsaturated bond represented by the reaction scheme:

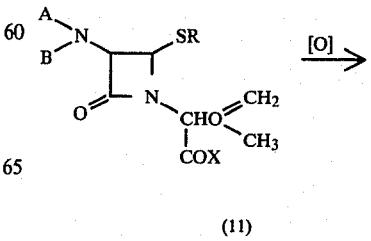

(11)

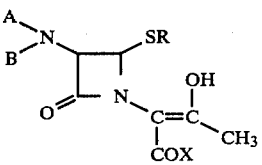

(12)

wherein A, B, R and X are as defined above.

The process is carried out by subjecting the said starting materials at the unsaturation in the substituent at position α to the oxidative cleavage to give the objective compounds.

For the oxidative cleavage are used ozone-oxidation: cemium tetroxide, hydrogen, peroxide-osumium tetroxide, sodium chlorate-osmium tetroxide, permanganates, to make glycol grouping, followed by glycol celavage; and other oxidative clearage, under condition where the other part of the molecule does not suffer unfavourable reactions, according to conventional methods.

Especially, ozone oxidation accompanies less side reactions, and it is preferable for its mild reaction condition. Ozone oxidation can be carried out by introducing ozone sufficient to form ozonide to a solution of the starting materials, followed by the action of reducing reagent capable of cleaving reductively the formed ozonide. Especially preferable solvents are alkane, haloalkane, ether, alkanoate ester, alkanoic acid, alcohol, aromatic hydrocarbon, solvents particularly a mixture of chloroalkane solvents and alcohol e.g. methanol, ethanol. The reducing reagents can be metal and acid (zinc and acetic acid, iron and hydrochloric acid, etc.), sulfur dioxide or sulfite (sodium sulfite, potassium hydrogen sulfite, etc.), trivalent phosphorous compound (phosphite ester, phosphite salt, etc.), ferrocyanide, sulfide (dialkyl sulfide e.g. dimethylsulfide, aromatic sulfide e.g. diphenyl sulfide, dibenzyl sulfide), hydrogen (in the presence of Raney nickel, platinum, palladium, etc.), borohydrides or their complex (sodium borohydride, etc.), aluminum hydride complex (lithium aluminum hydride, etc.), hydrazine, and ether reducing reagents. Formation of ozonide proceeds at a temperature lower than −80° C. or higher than room temperature, however, at lower temperature, efficacy of ozone is high and side reaction can be surpressed. Excess ozone can be removed from reaction medium by introduction of oxygen, nitrogen, air etc., to the reaction mixture. The reducing reagents can be added to the reaction mixture containing ozonide as it is or after suitable concentration of the mixture. The reaction with the reducing reagent can be carried out under conventional condition suitable for the used reagents.

Ozonization stated above can be replaced by subjecting the ozonide to hydrolysis, oxidation, termal decomposition, etc. to give objective compounds.

Following Examples illustrate the embodiments of this invention, but they shall not be taken to limit the scope thereof. The descriptions of the double bond linked to position 3 imply the presence of the position isomer with respect to the double bond linked to position 3.

PART I. Halogenation

Example 1.-I

One dissolves p-nitrobenzyl α-[3-phenoxymethyl-7-oxo-4-thia-2,6-diazabicyclo[3,2,0]hept-2-en-6-yl]-α-(1-hydroxyethylidene)acetate (939 mg) in tetrahydrofuran (14 ml), cools to −40° C., adds triethylamine (0.67 ml) and methanesulfonyl chloride (0.187 ml), stirs for 30 minutes at −40° C. and for 30 minutes at 0° C. To this solution, one adds morpholine (0.209 ml), stirs for 2 hours at 0° C., adds N-bromosuccinimide (393 mg), stirs for 1.5 hours at 0° C., dilutes with water (100 ml) and extracts with ethyl acetate. The obtained extract is washed with water, dried over sodium sulfate, and evaporated to give foam (1.349 g) which is purified by chromatography over silica gel containing 10% water to give p-nitrobenzyl α-[3-phenoxymethyl-7-oxo-α-4-thia-2,6-diazabicyclo[3,2,0]hept-2-en-6-yl]-α-methanesulfonyl-α-acetylacetate (81.7 mg; Yield: 7.5%), p-nitrobenzyl α-[3-phenoxymethyl-7-oxo-4-thia-2,6-diazabicyclo[3,2,0]hept-2-en-6-yl]-α-(1-morpholino-2-bromoethylidene)acetate (956.8 mg; 77.5%), and p-nitrobenzyl α-[3-phenoxymethyl-7-oxo-4-thia-2,6-diazabicyclo[3,2,0]hept-2-en-6-yl]-α-(1-morpholinoethylidene)acetate (120.5 mg; Yield: 11.2%).

Example 2.-I

One dissolves p-nitrobenzyl α-[3-phenoxymethyl-7-oxo-4-thia-2,6-diazabicyclo[3,2,0]hept-2-en-6-yl]-α-(1-hydroxyethylidene)acetate (940 mg) in dichloromethane (14 ml), cools to −25° C., adds triethylamine (0.61 ml) and methanesulfonyl chloride (0.17 ml), and stirs for 1.5 hours. To the solution, one adds morpholine (0.209 ml), keeps at −25° C. for 1.5 hours, adds bromine (2.2 mmol) dissolved in carbon tetrachloride (2.2 ml) and after 30 minutes at −25° C., adds 5% aqueous sodium hydrogen carbonate, washes with water, dries and evaporates. Purification of the obtained residue (1.134 g) by chromatography over silica gel containing 10% water (100 g) using a mixture of benzene and ethyl acetate (3:1) gives p-nitrobenzyl α-[3-phenoxymethyl-7-oxo-4-thia-2,6-diazabicyclo[3,2,0]hept-2-en-6-yl]-α-(1-morpholino-2-bromoethylidene)acetate (852.6 mg; 69%) and p-nitrobenzyl α-[3-phenoxymethyl-7-oxo-4-thia-2,6-diazabicyclo[3,2,0]hept-2-en-6-yl]-α-methanesulfonyl-α-acetylacetate (1332.2 mg; 12.2%).

Example 3.-I

One dissolves p-nitrobenzyl α-[4-methoxymethylthio-3-phenoxyacetamide-2-oxo-azetidin-1-yl]-α-(1-hydroxyethylidene)acetate (1.06 g) in tetrahydrofuran (10 ml), cools to −40° C. under nitrogen atmosphere, adds triethylamine (489 mg) dissolved in tetrahydrofuran (1 ml) and methanesulfonyl chloride (252 mg) dissolved in tetrahydrofuran (1 ml), and stirs for 30 minutes at −40° C. and for 45 minutes at 0° C. To this solution, one adds morpholine (209 mg) dissolved in tetrahydrofuran (1 ml), keeps at 0° C. for 2 hours, adds N-bromosuccimimide (392 mg), keeps at 0° C. for 1.5 hour, adds water, and removes the separated oily material, and extracts with ethyl acetate. The extract solution and the removed oily material is combined, dried over magnesium sulfate, and evaporated. Purification of the obtained residual oil (1.4 g) by chromatography over silica gel containing 5% water (20 g) gives p-nitrobenzyl α-[4-methoxymethylthio-3-phenoxyacetamido-2-oxo-azetidin-1-yl]-α-(1-morpholino-2-bromoethylidene)acetate (700 mg; Yield: 52%) and p-nitrobenzyl α-[4-methoxymethylthio-3-phenoxyacetamido-2-oxo-azetidin-1-yl]-α-(1-morpholinoethylidene)acetate (170 mg; Yield: 14%).

Stirring of the former product (100 mg) with 10% hydrochloric acid (0.3 ml) in a mixture of methanol (2 ml) and tetrahydrofuran (1 ml) at 0° C. for 90 minutes, followed by isolation by diluting with water, evaporating, dissolving in chloroform, washing with water, drying over magnesium sulfate, and evaporating gives p-nitrobenzyl α-[4-methoxymethylthio-3-phenoxyacetamido-2-oxo-azetidin-1-yl]-α-(1-hydroxy-2-bromoethylidene)acetate (70 mg). Yield: 78%.

Example 6.-I

One dissolves p-nitrobenzyl α-[3-benzyl-7-oxo-4-thia-2,6-diazabicyclo[3,2,0]hept-2-en-6-yl]-α-(1-hydroxyethylidene)acetate (827 mg) in methylene chloride (10 ml), cools to −20° C., adds a solution of methanesulfonyl chloride (1 M in methylene chloride; 2.2 ml) and a solution of triethylamine (1 M in methylene chloride; 2.2 ml), stirs for 90 minutes, cools to −25° C., adds morpholine (0.35 ml), stirs for 65 minutes, adds N-bromosuccinimide (340 mg), and stirs for 1 hour. One washes the reaction mixture with water, dries over magnesium sulfate, and evaporates. Purification of the

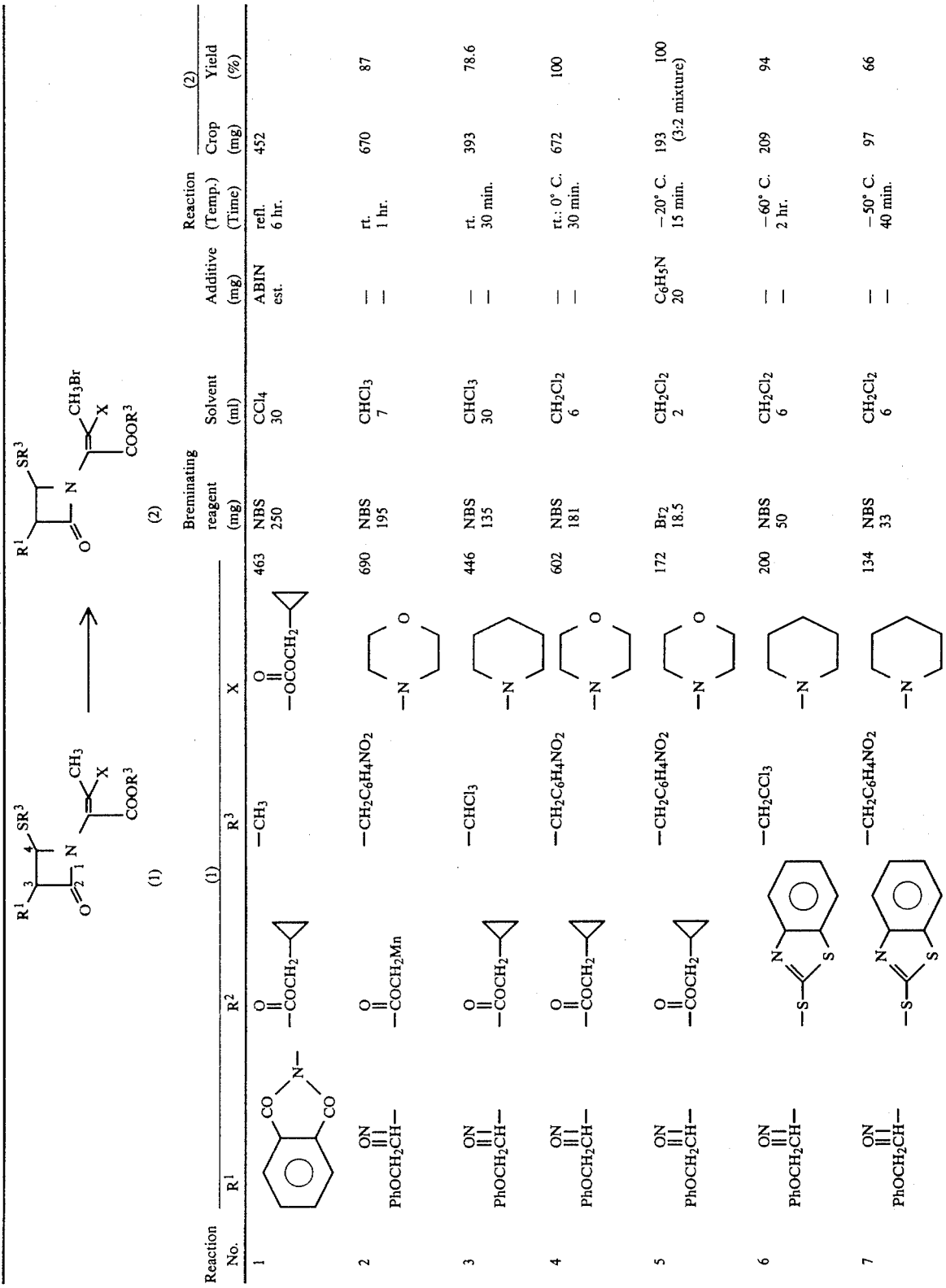

TABLE I (No. 1)-continued $$\underset{(1)}{\overset{R^1}{\underset{O}{\bigsqcup}}\overset{SR^3}{\underset{N}{\bigsqcup}}\overset{CH_3}{\underset{COOR^3}{C=}}X} \longrightarrow \underset{(2)}{\overset{R^1}{\underset{O}{\bigsqcup}}\overset{SR^3}{\underset{N}{\bigsqcup}}\overset{CH_2Br}{\underset{COOR^3}{C=}}X}$$

| Reaction No. | R¹ | R² | (1) | R³ | X | Brominating reagent (mg) | Solvent (ml) | Additive (mg) | Reaction (Temp.) (Time) | Crop (mg) | (2) Yield (%) |
|---|---|---|---|---|---|---|---|---|---|---|---|
| 8 | CH₂OPh<br>—N=C— | | 762 | —CH₂CCl₃ | morpholinyl-O | NBS 278 | CHCl₂ 40 | — | 0° C.<br>1 hr. | 537 | 61.2 |
| 9 | CH₂OPh<br>—N=C— | | 234 | —CH₂C₆H₄NO₂ | morpholinyl-O | NBS 83 | CHCl₂ 3 | — | rt.<br>80 min. | 166 | 62 |
| 10 | CH₂Ph<br>—N=C— | | 200 | —CH₂CCl₃ | morpholinyl-O | NBS 80 | CHCl₂ 10 | — | 0° C.<br>30 min. | 166 | 62 |
| 11 | CH₂OPh<br>—N=C— | | 312 | —CH₂C₆H₄NO₂ | —OCOC₇H₇ (mixed anhydride) | Br₂ 40 | THF + CCl₄<br>2 + 0.5 | LHDS 1.4 mmol | −70° C.<br>1 hr. | 23 | — |
| 12 | CH₂OPh<br>—N=C— | | 494 | —CH₂C₆H₄NO₂ | —OCOCH₂-cyclopropyl | Br₂ 40 | THF + CCl₄<br>8.6 + 0.96 | LHDS 1.3 mmol | −70° C.<br>40 min. | 197 | 35 |

(In the TABLE I, ABIN is for azobisisobutyrenitrile; est. is for catalytic amount; Hr is for hour; min. is for minutes; NBS is for N—bromosuccinimide; refl. is for reflex; rt. is for room temperature; THF is for tetrahydrofuran; and LHDS is for lithium homomethyldisiloxane)

TABLE II $$\text{structure: } R_1\text{-(azetidinone ring with SR}_2\text{)-N-C(=CH(OH)_2Br)(X)(COOR_3)}$$

| Compound No. | $R_1$ | $R_2$ | $R_3$ | X | mp (°C.) | IR:($\nu_{max}^{CHCl_3}$ cm$^{-1}$) | NMR($\delta$ CDCl$_3$) (Numbers in parentheses show coupling constants: Ns) |
|---|---|---|---|---|---|---|---|
| 1. | phthalimido (benzene-1,2-dicarboximide) | O=C(COOH$_2$)— | —CH$_3$ | —OCOOH$_2$-cyclopropyl | 137–140° C. | 1800,1795,1740. | 0.05–1.6mlOH,3.80–4.30mN,3.90s3N,4.50+4.72ABq(10)1M,4.92s1N,5.95d(5)1N,6.25d(5)1N,7.60m4N. |
| 2 | PhOCH$_2$CH(N=O)— | O=C(COCH$_2$Ph)— | —CH$_2$C$_6$H$_4$NO$_2$ | morpholino | Foam | 3400,1782,1720–1600. | 3.00–3.50m4N,3.50–3.90m4N,4.30&2N,4.47s2N,5.00–5.34m5N,5.50d(5)+5.77d(5)1H(Cn 3:2),6.70–8.25n 15H. |
| 3 | PhOCH$_2$CH(N=O)— | O=C(COCH$_2$-cyclopropyl)— | —CH$_2$CCl$_3$ | piperidino | — | 3440,1780,1700, 1550,1150. | 0.2–1.3mlH,1.72brs4H,3.98d(12)2H,4.55s 2H,4.75s2H,4.33–4.70m2H,5.17–5.58m1N,5.72d(5)+5.92d(6)1N,6.80–7.53m6N. |
| 4 | PhOCH$_2$COH(N=)— | O=C(COCH$_2$-cyclopropyl)— | —CH$_2$C$_6$H$_4$NO$_2$ | piperidino | Yellow Foam | 3426,1779,1695, 1603,1145. | 0.23–1.27m5H,3.16–3.59m4N,3.74–3.98m4N,4.05d(6)2H 4.50–4.71m4N,5.07–5.40m3N,5.8044(10.5)1N,6.72–8.33 m9H. |
| 5 | PhOCH$_2$CH(N=O)— | —COOCH$_2$-cyclopropyl | —CH$_2$C$_6$H$_4$NO$_2$ | —OH | — | 3426,1781,1710–1690,1601,1148. | 0.23–1.27m5H,4.01d(7)2N,4.27+4.35d2N4.55s2H 5.10–5.35m3N,3.89d(5)1N,6.83–7N,8.22d(9) 2M. |
| 6 | PhOCH$_2$CH(N=O)— | benzothiazol-2-ylthio (—S—) | —CH$_2$C$_6$H$_4$NO$_2$ | piperidino | — | 3440,1780,1695 1600. | 1.67brs6N,3.33brs4N,5.4m4N,5.0–5.5m4N,6.8–8.2n 14N. |
| 7 | PhOCH$_2$CH(N=O)— | benzothiazol-2-ylthio (—S—) | —CH$_2$CCl$_3$ | piperidino | — | 3440,1781,1698, 1600. | 1.60brs6N,3.38brs4N,4.4–4.9m6N,5.0–5.8m2N,6.8–8.0m10N. |

TABLE II-continued

Structure:
R₁, SR₂ substituents on β-lactam with N-CH(X)(CH(OH)(CH₂Br))COOR₃

| Compound No. | R₁ | R₂ | R₃ | X | mp (°C) | IR:($\nu_{max}^{CHCl_3}$ cm$^{-1}$) | NMR($\delta$CDCl₃) (Numbers in parentheses show coupling constants: Ns) |
|---|---|---|---|---|---|---|---|
| 8 | CH₂OPh / —N=C— | | —CH₂C₆N₄NO₂ | —OCC₆N₄NO₂ (O=C-O) | Oil | 1795,1700. | 2.5s3N,4.22+4.71ABq(14)2N,4.81s2N,5.19-2N,3.75s1N. |
| 9 | CH₂OPh / —N=C— | | —CH₂C₆N₄NO₂ | —OOOCH₂-cyclopropyl (O=C-O) | Foam | 1785,1732,1600 1172. | 0.30–1.67m3N,3.80–4.72m6N,5.27s2N,5.97d3N, 6.77–7.53m7N,0.17d2N. |
| 10 | CH₂OPh / —N=C— | | —CH₂C₆N₄NO₂ | morpholino | Yellow oil | 1775,1690. | 3.30m4N,3.43m4N,4.50+4.95ABq(14)2N,4.87s2N,3.25s 2N,5.75+5.96ABq(4)2N,6.66–3.13m3N. |
| 18 | CH₂OPh / —N=C— | | —CH₂CCl₃ | morpholino | — | 1780,1700,1615, 1550. | 3.05–3.95m8N,4.67ABq2N,4.78ABq2H,4.95s2N,5.83–6.15m 2N,6.82–7.48m5H. |
| 19 | CH₂OPh / —N=C— | | —CH₂CCl₃ | morpholino | — | 1780,1700,1615, 1600,1550. | 2.85–3.25m4N,3.25–3.82m4N,3.89s2N,4.29–5.02m4N,5.72– 5.92m2N,7.25s5N. |
| 20 | PhOCH₂CH(N=O)— | —CH₂OCH₃ | —CH₂C₆H₄NO₂ | morpholino | — | 3425,1770,1693, 1600. | 3.21s3H,3.39m4N,3.37m4N,4.4–4.7m6N,5.2–5.5m4N,6.8– 8.3s1OH. |
| 21 | PhOCH₂CH(N=O)— | —CH₂OCH₃ | —CH₂C₆H₄NO₂ | —OH | — | 3425,1775,1694, 1600. | 3.43s3H,4.30m2N,4.5–4.7m4N,5.2–5.5m4N,6.0–8.3m1OH, 12.2s1/2N. |
| 22 | CH₂OPh / —N=C— | | —CH₂C₆N₄NO₂ | morpholino | — | 1774,1695,1605. | 3.34m4N,3.69m4N,4.59+4.87ABq(14)2N,4.83s2N,5.233s2N, 5.77+6.00ABq(4)2N,6.80–8.20m9N. |

Chlorination obtained residue by chromatography over silica gel containing 10% water (30 g) gives p-nitrobenzyl α-[3-benzyl-7-oxo-4-thia-2,6-diazabicyclo[3,2,0]hept-2-en-6-yl]-α-(1-morpholino-2-bromoethylidene)acetate (710 mg). Yield: 65%.

Example 5.-I

One dissolves an azetidineacetic acid derivatives (1) in a solvent, if required adds an additive, adds a brominating reagent, and lets react for given time at given temperature. One washes the solution with water, dries, and evaporates.

Purification of the obtained residue by chromatography over silica gel containing 10% water, and evaporation of the fractions containing the objective compound gives the brominated azetidineacetic acid derivative (2).

The reaction conditions are given in TABLE I, and the physical constants are given in TABLE II.

Example 6.-I

In a procedure similar to these described in Examples 1 to 5, the following compounds are prepared:

(1) p-nitrobenzyl α-[4-cyclopropylmethoxycarbonylthio-3-thienylacetamido-2-oxo-azetidin-1-yl]-α-(1-morpholino-2-bromoethylidene)acetate.

(2) 2,2,2-trichloroethyl α-[4-methylsulfonylethylthio-3-carbobenzoxyamine-2-oxo-azetidine-1-yl]-α-(1-piperidino-2-bromoethylidene)acetate.

(3) phenacyl α-[4-ethoxycarbonylmethylthio-3-(2,2,2-trichloroethoxycarbonyl)amino-2-oxo-azetidine-1-yl]-α-(1-morpholino-2-bromoethylidene)acetate;

(4) sodium α-[4-isobutyrylthio-3-(o-nitrophenylsulfonyl)amino-2-oxo-azetidin-1-yl]-α-(1-acetoxy-2-bromoethylidene)acetate;

(5) pivaloyloxymethyl α-[4-benzoylthio-3-(N-tertiary butoxycarbonyl-α-phenylglycinamido)-2-oxo-azetidin-1-yl]-α-(1-dimethylamine-2-chloroethylidene)acetate;

(6) 2,2,2-trichloroethyl α-[4-chloroacetylthio-3-(N-trichloroethoxycarbonyl-α-phenylglycinamide)-2-oxo-azetidine-1-yl]-α-(1-chloro-2-bromoethylidene)acetate;

(7) α-[4-benzylthio-3-(2,2-dimethyl-4-phenyl-5-oxoimidazolidin-1-yl)-2-oxo-azetidin-1-yl]-α-(1-methoxy-2-bromoethylidene)-acetic acid;

(8) 2,2,2-trichloroethyl α-[4-anilinothio-3-(o-hydroxybenzylidene)-amino-2-oxo-azetidine-1-yl]-α-(1-diphenylphosphinyl-2-bromoethylideneacetate; and (9) α-[3-methyl-7-oxo-4-thia-2,6-diazabicyclo[3,2,0]hept-2-en-6-yl]-α-(1-chloro-2-bromoethylidene)acetic acid diisopropylhydrazide;

Example 7.-I

One dissolves p-nitrobenzyl α-[3-phenoxymethyl-7-oxo-4-thia-2,6-diazabicyclo[3,2,0]hept-2-en-6-yl]-α-(1-hydroxyethylidene)acetate (940 mg) in tetrahydrofuran (14 ml), adds triethylamine (0.61 ml) and methanesulfonyl chloride (0.172 ml), and stirs for 1 hour at −15° to −20° C. To the produced solution of p-nitrobenzyl α-[3-phenoxymethyl-7-oxo-4-thia-2,6-diazabicyclo[3,2,0]hept-2-en-6-yl]-α-(1-methanesulfonyloxyethylidene)-acetate, one adds morpholine (0.209 ml), stirs for 1.5 hours at −15° to −20° C., and for 2 hours at 0° C., to give a solution of p-nitrobenzyl α-[3-phenoxymethyl-7-oxo-4-thia-2,6-diazabicyclo[3,2,0]hept-2-en-6-yl]-α-(1-morpholinoethylidene)acetate, cools to −15° C., adds pyridine (0.174 ml) followed by after 5 minutes a solution of bromine in carbon tetrachloride (1 mole/liter: 2.1 ml), stirs for 15 minutes at the same temperature, pours into water (50 ml), and extracts with ethyl acetate (50 ml). The extract solution is washed with water, dried over magnesium sulfate, and evaporated to give residue (1.7 g). Purification of the residue by chromatography over silica gel containing 10% water gives from the fractions eluted with a mixture of benzene and ethyl acetate (2:1) p-nitrobenzyl α-[3-phenoxymethyl-7-oxo-4-thia-2,6-diazabicyclo[3,2,0]-hept-2-en-6-yl]-α-(2-bromo-1-morpholinoethylidene)acetate (1.109 g; Yield: 89.7%) and p-nitrobenzyl α-[3-phenoxymethyl-7-oxo-4-thia-2,6-diazabicyclo[3,2,0]hept-2-en-6-yl]-α-(2-bromo-1-morpholinoethyl)-α-methanesulfonylacetate (85 mg; Yield: 7.7%).

Similar reaction using N,N-dimethylformamide (14 ml) in place of tetrahydrofuran gives the same products (910 mg; 73.6% and 100 mg; 9.0% respectively).

EXAMPLE 8-I

One suspends p-nitrobenzyl α-[3-benzyl-7-oxoethylidene)-2,6-diaza-4-thiabicyclo[3,2,0]hept-2-en-6-yl]-α-(1-hydroxyethylideneacetate (2.265 g) in anhydrous tetrahydrofurane (30 ml), adds dropwise a solution of triethylamine (1.11 g) and methanesulfonyl chloride (630 mg) in tetrahydrofuran (2 ml) at 1° to 2° C., and stirs for 25 minutes. To the produced solution of p-nitrobenzyl α-[3-benzyl-7-oxo-2,6-diaza-4-thiabicyclo[3,2,0-]hept-2-en-6-yl]-α-(1-methanesulfonyloxyethylidene-)acetate, one adds a solution of morpholine (480 mg) in tetrahydrofuran (2 ml), and stirs for 15 minutes to give a solution of p-nitrobenzyl α-[3-benzyl-7-oxo-2,6-diaza-4-thiabicyclo[3,2,0]hept-2-en-6-yl]-α-(1-morpholinoethylidene)acetate, cools to −20° C., adds pyridine (396 mg) and a solution of bromine in carbon tetrachloride (1 mole/liter: 5 ml), pours into diluted hydrochloric acid after 15 minutes, and extracts with ethyl acetate. The extract solution is washed with water, dried over magnesium sulfate, and evaporated. Purification of the obtained residue by chromatography over silica gel (50 g), from the fraction eluted with a mixture of benzene containing 10% ethyl acetate gives p-nitrobenzyl α-[3-benzyl-7-oxo-2,6-diaza-4-thiabicyclo[3,2,0]hept-2-en-6-yl]-α-(2-bromo-1-morpholinoethylidene)acetate (2.36 g). Yield: 78%.

The product without isolation from the solution can be diluted with 5% hydrochloric acid (10 mole equivalents) and methanol, and stirred at room temperature for 3 hours to give p-nitrobenzyl 7-phenylacetamido-3-hydroxy-3-cephem-4-carboxylate in more than 70% yield.

EXAMPLE 9-I

One dissolves diphenylmethyl α-[3-benzyl-7-oxo-4-thia-2,6-diazabicyclo[3,2,0]hept-2-en-6-yl]-α-(1-hydroxy-ethylideneacetate (4.84 g) in tetrahydroufran (60 ml), cools to −20° C., adds triethylamine (2.84 ml) with stirring, adds dropwise methanesulfonyl chloride (0.82 ml) to the yellow solution, and lets react for 30 minutes. To the produced solution of diphenylmethyl α-[3-benzyl-7-oxo-4-thia-2,6-diazabicyclo[3,2,0]hept-2-en-6-yl]-α-(1-methanesulfonyloxyethylidene)acetate, one adds morpholine (0.96 ml) at −40° C., stirs for 3.5 hours, adds pyridine (0.77 ml) to the produced solution of diphenylmethyl α-[3-benzyl-7-oxo-4-thia-2,6-diazabicyclo[3,2,0]hept-2-en-6-yl]-α-(1-morpholinoethylidene)acetate, cools to −40° C., adds bromine (0.49 ml), and stirs for 30 minutes, to give diphenylmethyl α-[3-benzyl-7-oxo-4-thia-2,6-diazabicyclo[3,2,0]hept-2-en-6-yl]-α-(2-bromo-1-morpholinoethylidene)acetate. To this solution, one adds dropwise 5% hydrochloric acid (72 ml) and methanol (60 ml), stirs for 3 hours at room temperature, and keeps in a refrigerator overnight. The reaction mixture is evaporated to give residue which is dissolved in methylene chloride, washed with water, dried over sodium sulfate, and evaporated. Purification of the obtained residue (5.83 g) by chromatography over silica gel containing 10% water (150 g) gives from the fraction eluted with a mixture of benzene and ethyl acetate (4:1) diphenylmethyl 7-phenylacetamido-3-hydroxy-3-cephem-4-carboxylate (3.51 g) by recrystallization from n-hexane. m.p. 93°–96° C. Yield: 70%. IR: $\nu_{max}^{CHCl_3}$ 3410, 1782, 1674, 1610 cm$^{-1}$. NMR: $\delta^{CDCl_3}$ 3.20s2H, 3.64s2H, 4.97d(4 Hz)1H, 5.66dd(9:4)1H, 6.77d(9 Hz)1H, 6.90s1H, 7.35 ml 5H.

EXAMPLE 10-I

One dissolves p-nitrobenzyl α-[3-benzyl-7-oxo-4-thia-2,6-diazabicyclo[3,2,0]hept-2-en-6-yl]-α-(1-morpholinoethylidene)acetate (452 mg) in methylene chloride (5 ml), adds N-bromosuccinimide (170 mg) at −20° C., stirs for 80 minutes, pours the solution into ice water, and extracts with methylene chloride. The extract solution is washed with water, dried over magnesium sulfate, and evaporated. Purification of the obtained residue (461 mg) by chromatography over silica gel (25 g) gives from the fraction eluted with a mixture of benzene and ethyl acetate (2:1)p-nitrobenzyl α-[3-benzyl-7-oxo-4-thia-2,6-diazabicyclo[3,2,0]hept-2-en-6-yl]-α-(2-bromo-1-morpholinoethylidene)acetate (289 mg). Yield: 54.5%. IR: $\nu_{max}^{CHCl_3}$ 1770, 1690, 1610 cm$^{-1}$. NMR: $\delta^{CDCl_3}$ 3.00–3.74m8H, 5.52s2H, 4.47+4.71 Abq(13 Hz)2H, 5.23s2H, 5.68d(4 Hz)1H, 5.94d(4 Hz)1H, 7.20–8.25m9H.

TABLE III

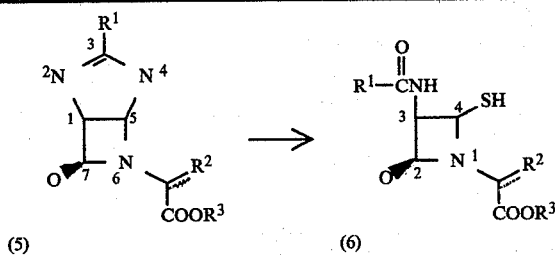

(5) → (6)

| Reaction No. | (5) R$^1$ | R$^2$ | R$^3$ | (mg) | Solvent ml | Acid ml | Temp. | Reaction Time (min) | (6) Crude Crop (mg) | Compound No. |
|---|---|---|---|---|---|---|---|---|---|---|
| 1 | PhOCH$_2$— | CH$_2$=C(OCH$_3$)— | —CH$_2$C$_6$H$_4$NO$_2$ | 200 | CH$_2$Cl$_2$ 4 (CH$_3$)$_2$CO 4 | 30% HClO$_4$ 0.8 | rt | 50 | 214 | 1 |
| 2 | PhOCH$_2$— | CH$_2$=C(OCH$_3$)— | —CH$_2$C$_6$H$_4$NO$_2$ | 200 | CH$_2$Cl$_2$ 4 (CH$_3$)$_2$CO 6 | 40% TsOH 0.5 | rt | 60 | 205 | 1 |
| 3 | PhOCH$_2$— | CH$_2$=C(CCH$_3$)— | —CH$_2$C$_6$H$_4$NO$_2$ | 200 | CH$_2$Cl$_2$ 4 (CH$_3$)$_2$CO 10 | 30% H$_3$PO$_4$ 1.0 | rt | 330 | 35 | 1 |
| 4 | PhOCH$_2$— | CH$_2$=C(CCH$_3$)— | —CH$_2$C$_6$H$_4$NO$_2$ | 200 | THF | 5 2NHCl 1.0 | rt | 50 | 105 | 1 |
| 5 | PhOCH$_2$— | CH$_2$=C(CCH$_3$)— | —CH$_2$C$_6$H$_4$NO$_2$ | 200 | CH$_2$Cl$_2$ 4 (CH$_3$)$_2$CO 10 | 30% CF$_3$COOH 1.0 | rt | 240 | 125 | 1 |
| 6 | PhOCH$_2$— | CH$_2$Br—C(=O)—N(morpholino) | —CH$_2$C$_6$H$_4$NO$_2$ | 227 | C$_6$H$_4$ 2 CH$_3$COOC$_2$H$_5$ 2 | 5% (COOH)$_2$ 4.0 | 70° C. | 30 | 10 | 6 |
| 7 | PhOCH$_2$— | CH$_3$—C(=COH)— | —CH$_2$C$_6$H$_4$NO$_2$ | 200 | CH$_2$Cl$_2$ 4 (CH$_3$)CO 4 | 30% HClO$_4$ 0.8 | rt | 35 | 220 | 2 |
| 8 | PhOCH$_2$— | CH$_3$—C(=COH)— | —CH$_2$CCl$_3$ | 293 | CH$_2$Cl$_2$ 5 (CH$_3$)$_2$CO 5 | 30% HClO$_4$ 1.0 | rt | 30 | 310 | 3 |
| 9 | PhOCH$_2$— | CH$_3$—C(=OCH$_3$)— | —CH$_2$C$_6$H$_4$NO$_2$ | 221 | THF | 5 30% HClO$_4$ 0.5 | rt | 45 | 231 | 4 |
| 10 | PhOCH$_2$— | —H | —C(CH$_3$)$_3$ | 200 | THF | 5 30% HClO$_4$ 1.0 | rt | 15 | 226 | 5 |

TABLE III-continued

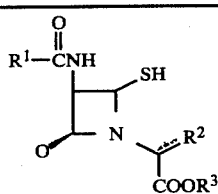

| Reaction No. | (5) R¹ | R² | R³ | (mg) | Solvent ml | Acid ml | Temp. | Reaction Time (min) | (6) Crude Crop (mg) | Compound No. |
|---|---|---|---|---|---|---|---|---|---|---|
| 11 | PhOCH₂— | CH₂Br, =O—N(morpholine) | —CH₂C₆H₄NO₂ | 227 | CH₂Cl₂ 4, (CH₃)₂CO 4 | 30% HClO₄ 0.8 | rt | 15 | 192 | 6 |
| 12 | PhCH₂— | CH₂=, —CCH₃ (||) | —CH₂C₆H₄NO₂ | 200 | THF 5 | 30% HClO₄ 0.5 | rt | 50 | 221 | 7 |

Ph is for phenyl;
THF is for tetrahydrofuran;
rt is for room temperature;
and TsOH is for toluene-p-sulfonic acid

TABLE IV $$R^1-\overset{O}{\underset{}{C}}NH \cdots \text{(structure with SH, N-R^2, COOR^3, O)}$$

| Compound No. | R¹ | R² | R³ | m.p. | IR: $\nu_{max}^{CHCl_3}$ | NMR: $\delta^{CDCl_3}$ (Numbers in parentheses show coupling constants in Hz) |
|---|---|---|---|---|---|---|
| 1. | PhOCH₂— | CH₂=, —CCH₃ (\|\|) | —CH₂C₆H₄NO₂ | 44–46° C. | 3415,2557, 1776,1748, 1693,1517. | 1.93s3H,2.12d(8.5)1H,4.57s2H,4.87s1H, 5.17brs1H,5.29s2H,ea.5.5m2H,6.83–8.25m10H. [α]$_D^{23}$−74.2° (c=0.271, CHCl₃). |
| 2. | PhOCH₂— | CH₃, =COH | —CH₂C₆H₄NO₂ | Foam | 3425,2568, 1776,1692, 1522. | 2.13d(9)1H,2.20s3H,4.55s2H,3.30s2H,ea.5.30m2H, 6.78–8.20m10H,12.60s1H. |
| 3. | PhOCH₂— | CH₃, =COH | —CH₂CCl₃ | Foam | 3425,2565, 1779,1694, 1519. | 2.10d(9.5)1H,2.26s3H,4.90+4.55ABq(12)2H,5.82– 5.05m2H,6.73–7.40m6H,11.92s1H. |
| 4. | PhOCH₂— | CH₃, =CCH₃ | —CH₂C₆H₄NO₂ | Foam | 3425,2564, 1773,1726, 1693,1522. | 2.12d(9)1H,2.25+2.08s+s6H,4.50s2H,5.20s2H,5.35– 5.08m2H,6.70–8.10m10H. |
| 5. | PhOCH₂— | —N | —C(CH₃)₃ | Semisolid | 3415,2350, 1775,1740, 1694,1513. | 1.45s9H,2.00d(10)1H,4.08+3.58ABq(17)2H,4.49s2H, 5.15dd(4.5;10)1H,5.55dd(4.5;8)1H,6.70–7.35m3H, 7.83d(8)1H. |
| 6. | PhOCH₂— | CH₂Br, =CON | —CH₂C₆H₄NO₂ | Foam | 3400,1780, 1692,1610, 1603. | 2.25d(10)1H,4.25d(2)2H,4.58s2H,5.20–5.37m4H, 6.84–8.24m9H,12.1s1H. |
| 7. | PhCH₂— | CH₂=, —CON₃ (\|\|) | —CH₂C₆H₄NO₂ | Foam | 3418,2550, 1771,1747, 1678,1521. | 1.87s3H,2.05d(8)1H,3.58s2H,4.77s3H,4.95s1H, 5.10brs1H,5.27s2H,7.10–8.12m10H,5.4m2H. |

PART II. Deprotection

EXAMPLE 1-II

To a solution of 3-phenoxymethyl-7-oxo-4-thia-2,6-diazabicyclo[3,2,0]hept-2-ene (200 mg) in a mixture of methylene chloride (8 ml) and acetone (8 ml) is added 30% perchloric acid aqueous solution (1.0 ml), and the mixture is stirred for 40 minutes at room temperature.

After diluting with excess water, the reaction mixture is extracted with methylene chloride. The extract solution is washed with water, dried over sodium sulfate, and concentrated. The white crystalline residue is 4β-mercapto-3β-phenoxyacetamido-2-oxozetidine, m.p. 137°–138° C. $[\alpha]_D^{23}+38.0\pm3.0°$ [c=0.261, CHCl$_3$+C$_2$H$_5$OH(4:1)]. IR: $\nu_{max}^{Nujol}$ 3290, 3200, 2562, 1757, 1658, 1549 cm$^{-1}$. NMR: $\delta^{d6-DMSO}$ 3.17brs1H, 4.58s2H, 5.00brs1H, 5.32dd(9:5 Hz)1H, 6.80–7.43m6H.

EXAMPLE 2-II

To a solution of α-[3-substituted (R$^1$)-7-oxo-4-thia-2,6-diazabicyclo[3,2,0]hept-2-en-6-yl]-α-substituted (R$^2$)-acetic acid ester (R$^3$)(5) in a solvent is added an acid, and the mixture is stirred at specified temperature for specified time. The reaction mixture is diluted with water, and extracted with methylene chloride. The extract solution is washed with water, dried over sodium sulfate, and evaporated to give objective α-[4-mercapto-3-substituted amino (R$^1$CONH-)-2-oxoazetidin-1-yl]-α-substituted (R$^2$)acetic acid ester (R$^3$) (6).

Table II shows reaction conditions, and Table IV shows the physical constants of the product (6). In Table II, the crude yield means weight of the products. They are almost pure when analyzed by thin-layer chromatogram and NMR-spectrum. Some of them were purified to give crystals.

In Reactions No. 3 and 6, the objective compounds were obtained in low yield, accompanied by a large amount of the starting materials and by-products.

EXAMPLE 3-II

To a solution of p-nitrobenzyl α-[3-phenoxymethyl-7-oxo-4-thia-2,6-diazabicyclo[3,2,0]hept-2-en-6-yl]-α-isopropenylacetate (200 mg) in tetrahydrofuran (5 ml) are added oxalic acid (200 mg) and water (0.5 ml), and the mixture is stirred at room temperature for 3 hours. The chromatogram of the reaction mixture shows the presence of p-nitrobenzyl α-[4-mercapto-3-phenoxyacetamido-2-oxo-azetidin-1-yl]-α-isopropenylacetate and the starting material.

EXAMPLE 4-II

In a procedure similar to Example 2.-II, the following compounds are prepared:
(1) 4-mercapto-3-thienylacetamido-2-oxo-1-acetylazetidine from 6-acetyl-3-thienylmethyl-7-oxo-4-thia-2,6-diazabicyclo[3,2,0]-hept-2-ene;
(2) 4-mercapto-3-benzamido-2-oxo-1-trifluoroacetylazetidine from 6-trifluoroacetyl-3-phenyl-7-oxo-4-thia-2,6-diazabicyclo[3,2,0]-hept-2-ene;
(3) 4-mercapto-3-acetamido-2-oxo-1-methylazetidine from 3,6-dimethyl-7-oxo-4-thia-2,6-diazabicyclo[3,2,0]hept-2-ene;
(4) 4-mercapto-3-(α-phenyl-α-chloroacetamido)-2-oxo-1-carbethoxycarbonylazetidine from 6-carbethoxycarbonyl-3-phenylchloromethyl-7-oxo-4-thia-2,6-diazabicyclo[3,2,0]hept-2-ene;
(5) α-[4-mercapto-3-formamido-2-oxoazetidin-1-yl]-α-isopropylidene acetic acid from α-[7-oxo-4-thia-2,6-diazabicyclo[3,2,0]hept-2-en-6-yl]-α-isopropylideneacetic acid; and
(6) 4-mercapto-3-benzylthiocarbonylamino-2-oxo-1-p-toluenesulfonylazetidine from 3-benzylthio-6-p-toluenesulfonyl-7-oxo-4-thia-2,6-diazabicyclo[3,2,0]hept-2-ene.

PART III Deprotection and Cyclization

EXAMPLE 1-III (1) To a solution of methyl α-[4-cyclopropylmethoxycarbonylthio-3-phthalimide-2-oxoazetidin-1-yl]-α-(2-bromo-1-cyclopropylmethoxycarbonyloxyethylidene)-acetate (500 mg) in methylene chloride (20 ml) is added aluminum chloride (510 mg) at once and the mixture is stirred at room temperature. After 1 hour, the mixture is poured into cold 3% hydrochloric acid (20 ml), and extracted with methylene chloride. The extract solution is washed with water, dried over magnesium sulfate, and evaporated to give methyl α-[4-mercapto-3-phthlimido-2-oxoazetidin-1-yl]-α-(2-bromo-1-hydroxyethylidene)-acetate (252 mg). Yield: 72.5%. IR: $\nu_{max}^{CHCl_3}$ 1790, 1783, 1728, 1670, 1620 cm$^{-1}$. NMR: $\delta^{CDCl_3}$ 1.80d(11 Hz)1H, 3.87s3H, 4.22+4.56AB2(10 Hz)2H, 5.38dd (11; 5 Hz)1H, 5.70d(5 Hz)1H, 7.76m4H, 12.3s1H.

(2) Methyl α-[4-mercapto-3-phthalimido-2-oxoazetidin-1-yl]-α-(2-bromo-1-hydroxyethylidene)-acetate(a) is treated under following conditions to give methyl 3-hydroxy-7-phthalimido-3-cephem-4-carboxylate (b): m.p. 223°–226° C. IR: $\nu_{max}^{CHCl_3}$ 1797, 1779, 1728, 1667, 1616 cm$^{-1}$. NMR: $\delta_{max}^{CDCl_3}$ 3.26+4.50ABq(14(2H), 5.60s3H, 5.63+6.15ABq(4)2H, 7.16m4H.

(i) To a solution of (a) (80 mg) in benzene (8 ml) is added, N,N-dimethylaniline (20 mg), and the mixture is refluxed under nitrogen atmosphere. After 30 minutes, the reaction mixture is cooled, acidified with 5% hydrochloric acid, and is extracted with ethyl acetate. The extract solution is washed with water, dried over magnesium sulfate, and evaporated. The residue (71 mg) is mixed with ethyl acetate (1 ml) and left for a while to give (b)(25 mg). m.p. 223°–226° C. Yield: 38.9%.

(ii) A solution of (a)(150 mg) in hexamethylphosphorotriamide (1 ml) is stirred at room temperature for 1 hour. The reaction mixture is mixed with ice water (6 ml) and ether (0.5 ml), to separate crystals of (b) (50 mg) which can be collected by filtration. Yield: 40.8%.

(iii) A solution of (a) (200 mg) is brought on the precoated PLC plate (silica gel F-254) distributed by E. Merck AG., and developed with a mixture of benzene and ethyl acetate (2:1). The band of main product is extracted with ethyl acetate containing 3% methanol, and the extract is evaporated under reduced pressure. The residue is dissolved in chloroform, freed from insoluble material, and evaporated to give (b) (62 mg). Yield: 37.9%.

Methyl 3-oxo-7-phthalimidocephem-4-carboxylate (b) thus prepared by above methods is dissolved in dioxane, mixed with a solution of diazomethane in ether, and stirred for 1 hour at room temperature. The reaction mixture is evaporated under reduced pressure to give methyl 3-methoxy-7-phthalimido-3-cephem-4-carboxylate in nearly quantitative yield. Recrystallization from a mixture of acetone and ether gives pure crystals, m.p. 225°–227° C.

EXAMPLE 2-III (1) To a solution of 2,2,2-trichloroethyl α-[4-cyclopropylmethoxycarbonylthio-3-phenoxyacetamido-2-oxoazetidin-1-yl]-α-[2-bromo-1-(piperidin-1-yl)ethylidene]acetate (573 mg) in methanol (30 ml) is added 10% hydrochloric acid (7 ml), and the mixture is stirred at room temperature or at 40° to 45° C. After 30 minutes, the reaction mixture is poured into ice water, and is extracted with benzene. The extract solution is washed with water, dried, and evaporated to give 2,2,2-trichloroethyl α-[4-cyclopropylmethoxycarbonylthio-3-phenoxyacetamido-2-oxoazetidin-1-yl]-α-(2-bromo-1-hydroxyethylidene)-acetate (434 mg). Yield: 83.5%. IR: $\nu_{max}^{CHCl_3}$ 3450, 1790, 1720, 1720 (sh), 1700 cm$^{-1}$. NMR: $\delta^{CDCl_3}$ 0.1–1.4m7H, 3.98d(7 Hz)2H, 4.27d(5 Hz)2H, 4.57s2H, 4.82d(3 Hz)2H, 5.27d(6;8 Hz)1H, 5.93d(5 Hz)1H, 6.8–7.5m6H, 11.67bra1H.

(2) To a stirred solution of 2,2,2-trichloroethyl α-[4-cyclopropylmethoxycarbonylthio-3-phenoxyacetamido-2-oxoazetidine-1-yl]-α-(2-bromo-1-hydroxyethylidene)acetate (330 mg) in methylene chloride (6 ml) is added aluminum chloride (330 mg) at room temperature, and the mixture is stirred for 60 minutes. The reaction mixture is poured into ice cold diluted hydrochloric acid, and is extracted with ethyl acetate. The extract solution is washed with diluted hydrochloric acid and water, dried, and evaporated to give 2,2,2-trichloroethyl 7-phenoxyacetamido-3-oxocephem-4-carboxylate (300 mg). Foam. IR: $\nu_{max}^{CHCl_3}$ 3420, 1780, 1685 cm$^{-1}$. NMR: $\delta^{CDCl_3}$ 3.37s2H, 4.53s2H, 4.85s2H, 5.07d(4)1H, 5.20–5.73m2H, 6.8–7.7m6H.

EXAMPLE 3-III

By a method similar to that described in Example 2.-III (1), 2,2,2-trichloroethyl α-[4-carbobenzoxythio-3-phenoxyacetamide-2-oxoacetidin-1-yl]-α-[2-bromo-1-(piperidin-1-yl)ethylidene]-acetate is hydrolyzed in methanolic hydrochloric acid to give 2,2,2-trichloroethyl α-[4-carbobenzoxythio-3-phenoxyacetamido-2-oxoazetidine-1-yl]-α-(2-bromo-1-hydroxyethylidene)acetate, and the product is cyclized with aluminum chloride in methylene chloride to give 2,2,2-trichloroethyl 7-phenoxyacetamido-3-oxocephem-4-carboxylate, identical with the product of Example 2.-III(2).

EXAMPLE 4-III (1) To a solution of p-nitrobenzyl α-[4-cyclopropylmethoxycarbonylylthio-3-phenoxyacetamido-2-oxoazetidine-1-yl]-α-[2-bromo-1-(morpholin-4-yl)ethylidene]acetate (300 mg) in a mixture of methanol (22 ml) and methylene chloride (3.5 ml), and the mixture is stirred at room temperature under nitrogen atmosphere after addition of 10% hydrochloric acid (4 ml). After 2 hours, the reaction mixture is poured into ice water, and is extracted with chloroform. The extract solution is washed with water, dried, and evaporated to give p-nitrobenzyl 4-cyclopropylmethoxycarbonylthio-3-phenoxyacetamido-2-oxo-α-(2-bromo-1-hydroxyethylidene)azetidine-1-acetate (252 mg). Foam. Yield: 92.8%. IR: $\nu_{max}^{CHCl_3}$ 3426, 1781, 1710, 1690, 1601 cm$^{-1}$. NMR: $\delta^{CDCl_3}$ 0.23–1.33m5H, 3.84–4.36m4H, 4.55s2H, 5.10–5.32m3H, 5.88d(5 Hz)1H, 6.83–8.33m9H, 12.0s1H.

(2) To a solution of p-nitrobenzyl α-[4-cyclopropylmethoxycarbonylthio-3-phenoxyacetaido-2-oxoazetidin-1-yl]-α-(2-bromo-1-hydroxyethylidene)acetate (218 mg) in methanol free methylene chloride (2.1 ml) is added aluminum chloride (220 mg) under ice cooling, and the mixture is stirred under argon atmosphere. After 35 minutes, the reaction mixture is poured into ice water containing 4N-hydrochloric acid (4 ml), stirred for 10 minutes, and is extracted with chloroform. The extract solution is washed with water, dried and evaporated to give p-nitrobenzyl α-[4-mercapto-3-phenoxyacetamido-2-oxoazetidin-1-yl]-α-(2-bromo-1-hydroxyethylidene)acetate (150 mg). Yellow foam. Yield: 94.6%. IR: $\nu_{max}^{CHCl_3}$ 3400, 1780, 1692, 1610, 1603 cm$^{-1}$. NMR: $\delta^{CDCl_3}$ 2.25d(10 Hz)1M, 4.25d(2 Hz)2H, 4.58s2N, 5.20–5.37m4H, 6.84–8.24m9H, 12.1s1H.

(3) To a solution of p-nitrobenzyl α-[4-mercapto-3-phenoxyacetamido-2-oxoacetidin-1-yl]-α-(2-bromo-1-hydroxyethylidene)acetate (106 mg) in benzene (5 ml) is added silica gel F-254 (500 mg) distributed by B. Merck Ag., and the mixture is shaken at room temperature for 1 hour. The insoluble material is removed by filtration, and washed several times with chloroform. The filtrate and washed solution are combined and evaporated under reduced pressure to give p-nitrobenzyl 3-hydroxy-7-phenoxyacetamido-3-cephem-4-carboxylate (60 mg). Yield: 66.3%. m.p. 95.5°–99.5° C. IR: $\nu_{max}^{CHCl_3}$ 3400, 1785, 1685, 1605. NMR: $\delta^{CDCl_3}$ 2.03s2H, 4.60s2H, 5.07+5.37ABq(4)2H, 5.37d(4)1H, 5.68dd(9;4)1H, 6.83–8.32m9H.

(4) A solution of p-nitrobenzyl α-[4-mercapto-3-phenoxyacetamido-2-oxoazetidin-1-yl]-α-(2-bromo-1-hydroxyethylidene)acetate (70 mg) prepared by the method of Example 4.-III(2) in a mixture of methylene chloride (2 ml) and methanol (2 ml) is stirred for 3 hours at room temperature. The reaction mixture is poured into ice water, and is extracted with methylene chloride. The extract solution is washed with water, dried over magnesium sulfate, and evaporated to give p-nitrobenzyl 3-hydroxy-7-phenoxyacetamido-3-cephem-4-carboxylate (42 mg), identical with the product of Example 4(3). Yield: 70%.

(5) A solution of p-nitrobenzyl α-[4-mercapto-3-phenoxyacetamido-2-oxoazetidin-1-yl]-α-(2-bromo-1-hydroxyethylidene)acetate prepared by the method of Example 4.-III(2) (70 mg) in a mixture of methylene chloride (2 ml), methanol (2 ml), and 10% hydrochloric acid (0.3 ml) is stirred at room temperature for 2 hours. The reaction mixture is poured into ice water, and is extracted with methylene chloride. The extract solution is washed with water, dried over magnesium sulfate, and evaporated to give p-nitrobenzyl 3-oxo-7-phenoxyacetamidocephem-4-carboxylate (44.5 mg), identical with the product of Example 4.-III(3). Yield: 74%.

EXAMPLE 5-III (1) A solution of p-nitrobenzyl α-[4-carbobenzoxythio-3-phenoxyacetamido-2-oxoazetidin-1-yl]-α-[2-bromo-1-(morpholin-4-yl)ethylidene]acetate (469 mg) in a mixture of methylene chloride (4 ml), methanol (4 ml), and 10% hydrochloric acid (0.8 ml) is stirred at room temperature for 2 hours. The reaction mixture is diluted with ice water, and is extracted with methylene chloride. The extract solution is washed with water, dried over magnesium sulfate, and evaporated to give p-nitrobenzyl α-[4-carbobenzoxythio-3-phenoxyacetamido-2-oxoazetidin-1-yl]-α-(2-bromo-1-hydroxyethylidene)acetate (426 mg). Yield: Quantitative. IR: $\nu_{max}^{CHCl_3}$ 3408, 1788, 1725, 1696, 1615, 1602 cm$^{-1}$. NMR: $\delta^{CDCl_3}$ 4.27d(3 Hz)2H, 4.48s2H, 5.16s2H, 5.22s2H, 5.29m1H, 5.86d(5 Hz)1H, 6.74–8.20m9H.

(2) To a solution of p-nitrobenzyl α-[4-carbobenzoxythio-3-phenoxyacetamido-2-oxoazetidin-1-yl]-α-(2-bromo-1-hydroxyethylidene)acetate (480 mg) in methylene chloride (5 ml) containing 20% of nitromethane is added a solution of aluminum chloride (270 mg) in methylene chloride containing 20% of nitromethane (4 ml), and the mixture is stirred at room temperature for 1 hour. The reaction mixture is poured into diluted hydrochloric acid, and is extracted with methylene chloride. The extract solution is washed water, dried over magnesium sulfate, and evaporated to give p-nitrobenzyl α-[4-mercapto-3-phenoxyacetamido-2-oxoazetidin-1-yl]-α-(2-bromo-1-hydroxyethylidene)acetate (376 mg). Yield: 99.5%.

EXAMPLE 6-III

To a solution of p-nitrobenzyl α-[4-cyclopropylmethoxycarbonylthio-3-phenoxyacetamido-2-oxoazetidin-1-yl]-α-[2-bromo-1-(morpholin-4-yl)ethylidene]acetate (151 mg) in methylene chloride (1.5 ml) is added aluminum chloride (0.42 mg) and the mixture is stirred for 50 minutes under ice cooling. The mixture is diluted with ice water (2 ml), stirred for 5 minutes, and stirred with a mixture (15 ml) of methanol and methylene chloride (5:1) after addition of 10% hydrochloric acid (3 ml) at room temperature for 80 minutes. The reaction mixture is diluted with ice water, and is extracted with chloroform. The extract solution is washed with water, dried over magnesium sulfate, and evaporated to give p-nitrobenzyl 3-hydroxy-7-phenoxyacetamido-3-cephem-4-carboxylate (63 mg). Yield: 63%. This product is identical with the product of Example 4.-III(3) produced by hydrolysis of the 4-morpholino group to be replaced with the corresponding hydroxy group.

EXAMPLE 7-III

In a procedure similar to these of the proceding Examples, following compounds are prepared:

(1) methyl 7-phthalimido-3-hydroxy-3-cephem-4-carboxylate, (2) 2,2,2-trichloroethyl 7-phenoxyacetamido-3-(morpholin-4-yl)-3-cephem-4-carboxylate, (3) p-methoxybenzyl 7-(2,2-dimethyl-3-nitroso-4-phenyl-5-oxoimidazolidin-1-yl)-3-hydroxy-3-cephem-4-carboxylate, (4) p-nitrobenzyl 7-(N-tertiary butoxycarbonyl-α-phenylglycyl)amino-3-oxocephem-4-carboxylate, (5) 2,2,2-trichloroethyl 7-thienylacetamido-3-hydroxy-3-cephem-4-carboxylate, (6) p-nitrobenzyl 7-salicylideneamino-3-hydroxy-3-cephem-4-carboxylate, (7) 2,2,2-trichloroethyl 7-benzyloxycarbonylamino-3-hydroxy-3-cephem-4-carboxylate, (8) p-nitrobenzyl 7-(2,2,2-trichloroethoxycarbonyl)amino-3-hydroxy-3-cephem-4-carboxylate.

EXAMPLE 8-III

To a solution of 2,2,2-trichloroethyl α-[3-phenoxymethyl-7-oxo-4-thia-2,6-diazabicyclo[3,2,0]hept-2-en-6-yl]-α-[2-bromo-1-(morpholin-4-yl)ethylidene]acetate (6.00 g) in a mixture of chloroform (150 ml) and methanol (200 ml) is added 10% hydro chloric acid (40 ml) at room temperature, and the mixture is stirred for 60 minutes. The reaction mixture is poured into ice water and extracted with chloroform. The extract solution is washed with water, dried, and evaporated to give 2,2,2-trichloroethyl 3-oxo-7-phenoxyacetamidocepham-4-carboxylate (4.70 g). Foam. Yield: 99.8%

EXAMPLE 9-III

To a solution of p-nitrobenzyl α-[3-phenoxymethyl-7-oxo-4-thia-2,6-diazabicyclo[3,2,0]hept-2-en-6-yl]-α-[2-bromo-1-(morpholin-4-yl)ethylidene]acetate (63 mg) in a mixture of methanol (4 ml) and methylene chloride (3 ml) is added 10% hydrochloric acid (0.38 ml), and the mixture is stirred at room temperature for 75 minutes. The reaction mixture is poured into ice water, and is extracted with methylene chloride. The extract solution is washed with water, dried over magnesium sulfate, and evaporated to give p-nitrobenzyl 3-hydroxy-7-phenoxyacetamido-3-cephem-4-carboxylate (41 mg). m.p. 95.5°–99.5° C. Yield: 82.9%.

EXAMPLE 10-III

To a solution of p-nitrobenzyl α-[3-phenoxymethyl-7-oxo-4-thia-2,6-diazabicyclo[3,2,0]hept-2-en-6-yl]-α-[2-chloro-1-(morpholin-4-yl)ethylidene]acetate (106 mg) in a mixture (6 ml) of methanol and methylene chloride (2:1) is added 2 N-hydrochloric acid (0.92 ml), and the mixture is stirred at room temperature under argon atmosphere. After 40 minutes, the reaction mixture is diluted with ice water, and is extracted with methylene chloride. The extract solution is washed with water, dried over magnesium sulfate, and evaporated to give yellow oil (94 mg). Purification of the oil by chromatography over thin-layer of silica gel gives from the fraction eluted with a mixture of benzene and ethyl acetate (1:2) p-nitrobenzyl 3-hydroxy-7-phenoxyacetamide-3-cephem-4-carboxylate (20 mg). Yield: 22%.

EXAMPLE 11-III

To a solution of 2,2,2-trichloroacetyl α-[3-benzyl-7-oxo-4-thia-2,6-diazabicyclo[3,2,0]hept-2-en-6-yl]-α[2-bromo-1-(morpholin-4-yl)ethylidene]acetate, (117 mg) in a mixture (4 ml) of methanol and chloroform (1:1) is added 10% hydrochloric acid (0.5 ml), and the mixture is stirred for 2 hours at room temperature. The reaction mixture is extracted with chloroform. The extract solution is washed with water, dried, and evaporated. The purification of the obtained residue by chromatography over silica gel gives 2,2,2-trichloroethyl 3-oxo-7-phenylacetamidocepham-4-carboxylate (41 mg). Yield: 44%. NMR: $\delta^{CDCl_3}$ 3.33s2H, 3.60s2H, 4.83s2H, 5.00d(5)1H, 5.13–5.70m2H, 6.82d(8)1H, 7.25m5H.

EXAMPLE 12-

To a solution of p-nitrobenzyl α-[3-benzyl-7-oxo-4-thia-2,6-diazabicyclo[3,2,0]hept-2-en-6-yl]-α-[2-bromo-1-(morpholin-4-yl)ethylidene]acetate (248 mg) in a mixture of methanol (8 ml) and methylene chloride (6 ml) is added 10% hydrochloric acid (1.5 ml) under ice cooling, and the mixture is stirred for 2 hours. The reaction mixture is poured into ice water, and is extracted with methylene chloride. The extract solution is washed water, dried over magnesium sulfate, and evaporated to give residue (184 mg). Purification of the residue by chromatography over silica gel containing 10% water (10 g) gives from the fraction eluted with a mixture of benzene and ethyl acetate (2:1) p-nitrobenzyl 7-phenylacetamide-3-hydroxy-3-cephem-4-carboxylate (66 mg). Oil. Yield: 35%. IR: $\nu_{max}^{CHCl_3}$ 3400, 1782, 1678, 1612. NMR: $\delta^{CDCl_3}$ 3.32d2H, 3.63s2H, 4.97d1H, 5.34dsH, 5.60q1H, 7.3m6H, 7.47–8.30q4H.

EXAMPLE 13-III

In a procedure similar to these of the preceding Examples, following compounds are prepared:

(1) 7-acetamide-3-oxocephem-4-carboxylic acid 1,2-diisopropylhydrazide, (2) diphenylmethyl 7-phenoxyacetamide-3-hydroxy-3-cephem-4-carboxylate, and (3) 7-phenylacetamido-3-hydroxy-3-cephem-4-carboxylic acid.

EXAMPLE 14-III

To a solution of p-nitrobenzyl α-[3-phenoxymethyl-7-oxo-4-thia-2,6-diazabicyclo[3,2,0]hept-2-en-6-yl]-α[2-bromo-1-(morpholin-4-yl)ethylidene]acetate (580 mg) in tetrahydrofuran (10 ml) is added 60% perchloric acid aqueous solution (1.5 ml) at −10° C., and the mixture is stirred for 30 minutes. The reaction mixture is diluted with water, and is extracted with methylene chloride. The extract solution is washed with water, dried over anhydrous sodium sulfate, and evaporated to give pale yellow foam (512 mg). The foam is purified by chromatography over silica gel containing 10% water (50 g) to separate from fractions eluted with a mixture of benzene and ethyl acetate (1:1) p-nitrobenzyl α-[3-phenoxymethyl-7-oxo-4-thia-2,6-diazabicyclo[3,2,0]hept-2-en-6-yl]-α-(2-bromo-1-hydroxyethylidene)acetate (foam: 207 mg: yield: 40%). IR: $\nu_{max}^{CHCl_3}$ 1781 cm$^{-1}$. NMR: $\delta^{CDCl_3}$ 3.75+3.95ABq(10 Hz)2H, 4.72s2H, 5.25s2H, 5.73d(4 Hz)1H, 6.07d(4Hz)1H, 6.73–8.15m9H, 12.07s1H.

From the fractions p-nitrobenzyl α-[3-phenoxyacetamido-4-mercapto-2-oxoazetidin-1-yl]-α-(2-bromo-1-hydroxyethylidene)-acetate can also be isolated as a by-product.

The former main product (84 mg) is dissolved in tetrahydrofuran (2 ml), mixed with 2N-hydrochloric acid (0.2 ml), and let stand at 0° C. for 30 minutes and at room temperature for 1 hour. The reaction mixture is diluted with water, and is extracted with methylene chloride. The extract solution is washed with water, dried over sodium sulfate, and evaporated. The residue (75 mg) can be identified with p-nitrobenzyl 7-phenoxyacetamido-3-oxocephem-4-carboxylate by IR- and NMR-spectroscopy.

EXAMPLE 15-III

One adds triethylamine (5.68 ml) to a stirred suspension of p-nitrobenzyl α-[3-benzyl-7-oxo-4-thia-2,6-diazabicyclo[3,2,0]hept-2-en-6-yl]-α-(1-hydroxyethylidene)acetate (9.06 g) in tetrahydrofuran (120 ml) under nitrogen atmosphere at −20° C. to give clear solution, adds methanesulfonyl chloride (1.65 ml) to the solution, stirs for 30 minutes at the same temperature, adds morpholine (1.92 ml), warms to 0° C., stirs for 5 hours, cools to −30° C. to −35° C., adds pyridine (1.54 ml) and bromine (3.12 g), stirs for 20 minutes, warms to ice-water temperatur, adds 5% hydrochloric acid (144 ml) and methanol (120 ml), stirs for 3 hours at room temperature, and 1 lets stand overnight at 0° C. Collection of the separated crystals in the reaction mixture by filtration gives p-nitrobenzyl 7-phenylacetamide-3-hydroxy-3-cephem-4-carboxylate (6.678g). m.p. 201° C. Yield: 71%.

(1) To a dry ice acetone cooled solution of diphenylmethyl α[3-phenoxymethyl-7-oxo-2,6-diaza-4-thiabicyclo[3,2,0]hept-2-en-6-yl]-α-(1-chloro-2-propen-2-yl)acetate (160 mg) in a mixture of methylene chloride (3.2 ml) and methanol (0.3 ml) is introduced ozone until the reaction mixture shows blue color. Then excess ozone is purged with oxygen, mixed with an aqueous solution of 95% sodium hydrogen sulfite (100 mg), warmed to room temperature to decompose the ozonide. After 1.5 hours, the solution is washed with 5% sodium hydrogen carbonate and water, dried, and concentrated to remove methylene chloride. The resultant oil (132 mg) is purified over thin-layer chromatographic plate (Merck 60F-254) using a mixture of benzene and ethyl acetate (1:1) as developing solvent to give diphenylmethyl α-[3-phenoxymethyl-7-oxo-2,6-diaza-4-thiabicyclo[3,2,0]-hept-2en-6-yl]-α-(2-chloro-1-hydroxyethylidene)acetate (44 mg) as glass.

IR: $\nu_{max}^{CHCl_3}$ 1784, 1672, 1620, 1603 cm$^{-1}$.

NMR: $\delta^{CDCl_3}$ 4.00s2H, 4.66+4.96ABq(14 Hz)2H, 5.23s2H.

(2) To an ice cooled solution of diphenylmethyl α-[3-phenoxymethyl-7-oxo-2,6-diaza-4-thiabicyclo[3,2,0-]hept-2-en-6-yl]-α-(2-chloro-1-hydroxyethylidene)acetate (36 mg) in a mixture of methanol and tetrahydrofuran (1:1) (1.1 ml) is added 1N-hydrochloric acid (0.39 ml), warmed to the room temperature, and the mixture is stirred for 1.5 hours. The reaction mixture is poured into ice water, and is extracted with methylene chloride. The extract solution is washed with 5% aqueous sodium hydrogen carbonate solution and water, dried over sodium sulfate, and evaporated. Purification of the obtained residue by thin-layer chromatography using a mixture of benzene and ethyl acetate (3:2) give diphenylmethyl 7-phenoxyacetamido-3-hydroxy-3-cephem-4-carboxylate (6 mg). m.p. 125°–126° C.

IR: $\nu_{max}^{CHCl_3}$ 3420, 1788, 1738, 1692, 1600 cm$^{-1}$.

NMR: $\delta^{CDCl_3}$ 3.33s2H, 4.54s2H, 5.02d(4 Hz)1H, 5.26s2H, 5.62dd(10:4 Hz)1H, 6.81∝7.45m 10H, 11.5brs1H.

EXAMPLE 16-III

To a solution of p-nitrobenzyl α-[3-benzyl-7-oxo-4-thia-2,6-diazabicyclo[3,2,0]hept-2-en-6-yl]-α-(2-bromo-1-dimethylaminoethylidene)acetate (380 mg) in tetrahydrofuran (10 ml) are added 5% sulfuric acid (2 ml) and methanol (10 ml), and the mixture is stirred for 2 hours at room temperature. The reaction mixture is kept at 0° C. overnight to separate p-nitrobenzyl 7-phenylacetamido-3-hydroxy-3-cephem-4-carboxylate (240 mg), m.p. 201° C.

TABLE

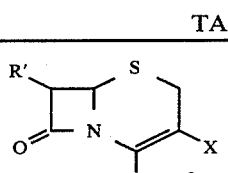

(Ph shows a phenyl group)

| Compound No. | R[1] | R[2] | X | m.p. | IR: $\nu_{max}^{CHCl_3}$ cm$^{-1}$ | NMR: $\delta^{CDCl_3}$ (Numbers in parenthesis show coupling constants in Ns) |
|---|---|---|---|---|---|---|
| 1 | OH<br>‖<br>PhOCH$_2$CN— | —CH$_2$CCl$_3$ | —OH | — | 3420,1780, 1685. | 3.37s2H,4.53s2H,4.85s2H,5.07d(4)1H, 5.20–5.73n2H,6.8–7.7m6H. |

TABLE-continued (structure shown: β-lactam fused with sulfur-containing ring, with R', S, N, O, COOR³, X substituents)
(Ph shows a phenyl group)

| Compound No. | R¹ | R² | X | m.p. | IR: $\nu_{max}^{CHCl_3}$ cm$^{-1}$ | NMR: $\delta^{CDCl_3}$ (Numbers in parenthesis show coupling constants in Ns) |
|---|---|---|---|---|---|---|
| 2 | PhOCH₂CN— with OH and ‖ | —CH₂C₆H₄NO₂—p | —OH | 95.5–99.5° C. | 3400,1785, 1685,1605. | 2.03s2H,4.60s2H,5.07 + 5.37ABq(4)2H, 5.37d(4)1H, 5.68dd(9;4)1H,6.83–8.32m9H. |
| 3 | PhCH₂CN— with OH and ‖ | —CH₂C₆H₄NO₂—p | —OH | — | 3400,1782, 1678,1612. | 3.32d2H,3.63s2H,4.97d1H,5.34dsH,5.60q1H, 7.3m6H,7.47–8.30q4H. |
| 4 | PhCH₂CN— with OH and ‖ | —CH₂CCl₃ | —OH | — | — | 3.33s2H,3.60s2H,4.83s2H,5.00d(5)1H, 5.13–5.70m2H,6.82d(8)1H,7.25m5H. |
| 5 | phthalimido (benzene ring with two CO groups attached to N—) | —CH₃ | —OH | 223–226° C. | 1797, 1779, 1728,1667, 1616. | 3.26 + 4.50ABq(14)2H,5.60s3H,5.63 + 6.15ABq(4)2H,7.16m4H. |

The table is for products of all Examples in part III and not for any specific example.

EXAMPLE 17-III

To a solution of p-nitrobenzyl α-[4-methoxymethylthio-3-phenoxyacetamido-2-oxoazetidin-1-yl]-α-(2-bromo-1-hydroxyethylidene)acetate (200 mg) in a mixture of dioxane (5 ml) and ethanol (2 ml) is added a solution of mercuric chloride (300 mg) in water (2 ml), and the mixture is stirred for 12 hours at 50° C. The reaction mixture is concentrated under reduced pressure, extracted with ethyl acetate, washed with water, dried and evaporated to give residue, which is dissolved in a mixture of methylene chloride and methanol, passed through a layer of silica gel, concentrated and treated with ether. The obtained foam is p-nitrobenzyl 7-phenoxyacetamido-3-hydroxy-3-cephem-4-carboxylate identical with authentic sample.

EXAMPLE 18-III

One adds to a solution of benzyl α-[3-benzyl-7-oxo-4-thia-2,6-diazabicyclo[3,2,0]hept-2-en-6-yl]-α-(1-hydroxyethylidene)acetate (1.424 g) in tetrahydrofuran (15 ml), triethylamine (0.96 ml), and methanesulfonyl chloride (0.28 ml) at −30° to −20° C., stirs for 55 minutes to give benzyl α-[3-benzyl-7-oxo-4-thia-2,6-diazabicyclo[3,2,0]hept-2-en-6-yl]-α-(1-methanesulfonyloxyethylidene)acetate, adds morpholine (0.40 ml) and stirs for 5 hours at −10° C. to +3° C. to give benzyl α-[3-benzyl-7-oxo-4-thia-2,6-diazabicyclo[3,2,0]hept-2-en-6-yl]-α-(1-morpholinoethylidene)-acetate, cools to −35° C. to −30° C., adds pyridine (0.27 ml) and bromine in carbon tetrachloride (1 mmole/ml: 3.2 ml), and stirs for 20 minutes to give benzyl α-[3-benzyl-7-oxo-4-thia-2,6-diazabicyclo[3,2,0]hept-2-en-6-yl]hept-2-en-6-yl]-α-(1-morpholino-2-bromoethylidene)acetate, adds 5% hydrochloric acid (13 ml) and methanol (50 ml), and kept at 0° C. overnight to hydrolyze and cyclize giving the cephem product. The solvent is removed under reduced pressure, and the residual solution is extracted with ethyl acetate. The extract solution is washed with saturated saline and water, dried over sodium sulfate, and purified by chromatography over silica gel containing 10% water. The fractions containing the product are combined and evaporated. Recrystallization of the residue from a mixture of methanol, ether, and hexane gives benzyl 7-phenylacetamido-3-hydroxy-3-cephem-4-carboxylate. m.p. 149°–162° C.

NMR: $\delta^{CDCl_3}$ 3.28d2H, 3.63s2H, 4.98d(5 Hz)1H, 5.30s2H, 5.60dd (5,8 Hz)1H, 6.37d(8 Hz)1H, 7.4s+7.4s10H, 11.6brs1H.

IR: $\nu_{max}^{CHCl_3}$ 3420, 1785, 1680, 1615 cm$^{-1}$.

EXAMPLE 19-III (i) To a solution of benzyl α-[3-phenoxymethyl-7oxo-4-thia-2,6-diazabicyclo[3,2,0]hept-2-en-6-yl]-α-isopropenylacetate (4.22 g) in dichloromethane and methanol (5:1) is introduced ozonized oxygen until the blue color of the solution does not fade out. Then the solution is mixed with dimethyl sulfide, washed with water, dried, and concentrated. The obtained residue is purified by chromatography over silica gel containing 10% water to give benzyl α-[3-phenoxymethyl-7-oxo-4-thia-2,6-diazabicyclo[3,2,0]hept-2-en-6-yl]-α-(1-hydroxyethylidene)acetate (2.98 g; 70.28%).

(ii) One adds triethylamine (1.42 ml), and methanesulfonyl chloride (0.41 ml) to a solution of benzyl α-[3-phenoxymethyl-7-oxo-4-thia-2,6-diazabicyclo[3,2,0-]hept-2-en-6-yl]-α-(1-hydroxyethylidene)acetate (2.12 g) in tetrahydrofuran (30 ml) at −30° C., stirs for 70 minutes to give benzyl α-[3-phenoxymethyl-7-oxo-4-thia-2,6-diazabicyclo[3,2,0]hept-2-en-6-yl]-α-(methanesulfonyloxyethylidene)acetate, adds morphline (0.6 ml) and stirs for 4 hours 50 minutes at 0° C. to give benzyl α-[3-phenoxymethyl-7-oxo-4-thia-2,6-diazabicyclo[3,2,0]hept-2-en-6-yl]-α-(1-morpholinoethylidene)acetate, cools to −50° C., adds pyridine (0.385 ml) and bromine (0.25 ml), and stirs for 30 minutes to give benzyl α-[3-phenoxymethyl-7-oxo-4-thia-2,6-bicyclo[3,2,0-]hept-2-en-6-yl]-α-(1-morpholino-2-bromoethylidene-)acetate, adds 5% hydrochloric acid (36 ml), methanol (42.5 ml), and tetrahydrofuran (12.5 ml) to give clear solution. The solution is concentrated, the resulting solution being extracted with ethyl acetate, washed with saturated saline, dried over sodium sulfate, and concentrated to give residue (2.31 g). Purification of the residue by chromatography over silica gel containing 10% water gives benzyl 7β-phenoxyacetamido-3-hydroxy-3-cephem-4-carboxylate (1.11 g). m.p. 126°–127° C.

PART IV Ozonolysis

EXAMPLE 1-IV

To a solution of methyl α-[4-acetylthio-3-phthalimido-2-oxoazetidin-1-yl]-α-isopropenyl acetate (200 mg) in methylene chloride (10 ml) is introduced excess ozone at −5° C. After the gas at the outlet makes a potassium iodide starch paper coloured, the reaction mixture is concentrated to 2 ml, mixed with a solution of sodium borohydride (50 mg) in methanol (10 ml), and stirred for 30 minutes. The reaction mixture is concentrated and dissolved in methylene chloride, washed with water, dried, and evaporated. The residue is crystallized from a mixture of methylene chloride and ether to give methyl α-[4-acetylthio-3-phthalimido-2-oxoazetidin-1-yl]-α-(1-hydroxyethylidene)acetate (157 mg). Yield: 78%. m.p. 178°–183° C.

EXAMPLE 2-IV

To a solution of α-[4-acetylthio-3-phthalimido-2-oxoazetidin-1-yl]-α-isopropenyl acetic acid (100 mg) in methanol (10 ml) at 0° C. is introduced excess ozone. After the gas at the outlet makes a potassium iodide starch paper coloured, the reaction mixture is bubbled with sulfur dioxide gas. The reaction mixture is concentrated, and the obtained residue is dissolved in aqueous solution of sodium hydrogen carbonate, washed with ether, neutralized with hydrochloric acid, and extracted with methylene chloride. The extract solution is washed with water, dried, and evaporated to give α-[4-acetylthio-3-phthalimido-2-oxoazetidin-1-yl]-α-acetyl-acetic acid (64 mg). Yield: 63%. Foam.

IR: $\nu_{max}^{CHCl_3}$ 1780, 1730, 1680 cm$^{-1}$.

EXAMPLE 3-IV

To a stirred solution of 2,2,2-trichloroethyl α-[4-(2-benzothiazolyl)dithio-3-phenoxyacetamido-2-oxoazetidin-1-yl]-α-isopropenyl-acetate (1.76 g) in a mixture of (methylene chloride (70 ml) and methanol (18 ml), is introduced ozone under cooling with dry ice acetone until the solution appears faint blue in color. After introducing nitrogen gas, the reaction mixture is treated with sulfur dioxide gas until the solution appears faint yellow in color (about 30 seconds), and is concentrated. The resulted residue is extracted with methylene chloride, washed with saline, dried, and concentrated to give powdery residue (1.35 g). Purification of the residue by chromatography over silica gel (30 g) gives 2,2,2-trichloroethyl α-[4-(2-benzothiazolyl)dithio-3-phenoxyacetamido-2-oxoazetidin-1-yl]-α-(1-hydroxyethylidene)-acetate (1.09 g; Yield: 62.0%; m.p. 130°–131° C.), and 2,2,2-trichloroethyl α-[4-(2-benzothiazolyl)-dithio-3-phenoxyacetamido-2-oxoazetidin-1-yl]-α-(1,1-dimethoxyethyl)-acetate (0.30 g; Yield: 15.6%).

TABLE V

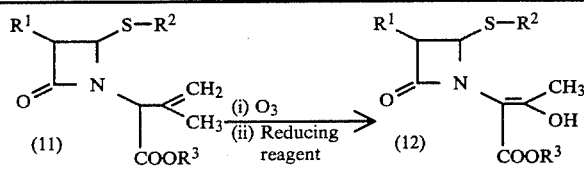

| Reaction number | (11) R$^1$ | R$^2$ | R$^3$ | (mg) | Solvent (ml) | Temperature (°C.) | Reducing reagent (ml) | (12) Crop (mg) | Yield (%) |
|---|---|---|---|---|---|---|---|---|---|
| 1 | phthalimido (structure) | —COCH$_3$ | —CH$_3$ | 15100 | CH$_2$Cl 300 | −30 | CH$_3$SCH$_3$ 6 | 10900 | 71.5 |
| 2 | PhOCH$_2$CN(H)(=O)— | —COCH$_3$ | —CH$_2$C$_6$H$_4$NO$_2$ | 5100 | CH$_2$Cl$_2$ + CH$_3$OH 200 + 50 | −70 | CH$_3$SCH$_3$ 5 | 4850 | 95.0 |
| 3 | PhOCH$_2$CN(H)(=O)— | —COCH$_3$ | —CHPh$_2$ | 4200 | CH$_2$Cl$_2$ + CH$_3$OH 50 + 50 | d.a. | CH$_3$SCH$_3$ 3 | 3100 | 74.0 |
| 4 | PhOCH$_2$CN(H)(=O)— | —COCH$_3$ | —CH$_2$CCl$_3$ | 8000 | CH$_2$Cl$_2$ + CH$_3$OH 240 + 80 | d.a. | CH$_3$SCH$_3$ 15 | 7800 | 97.0 |
| 5 | PhOCH$_2$CN(H)(=O)— | —COOCH$_2$–(cyclopropyl) | —CH$_2$C$_6$H$_4$NO$_2$ | 106 | CH$_2$Cl$_2$ + CH$_3$OH 5 + 1 | −30 | CH$_3$SCH$_3$ 0.2 | 103 | 97 |
| 6 | PhOCH$_2$CN(H)(=O)— | —CH$_2$COO–t-C$_4$H$_9$ | —CH$_2$C$_6$H$_4$NO$_2$ | 272 | CH$_2$Cl$_2$ + CH$_3$OH 10 + 3 | −78 | CH$_3$SCH$_3$ 1 | 218 | 80 |
| 7 | PhOCH$_2$CN(H)(=O)— | —S–(benzothiazolyl) | —CH$_2$C$_6$H$_4$NO$_2$ | 950 | CH$_2$Cl$_2$ 50 | d.a. | CH$_3$SCH$_3$ 0.8 | 540 | 56.7 |

TABLE V-continued $$\underset{(11)}{\overset{R^1}{\underset{O}{\overset{|}{\bigsqcup}}}\overset{S-R^2}{\underset{N}{\bigsqcup}}\overset{CH_2}{\underset{CH_3}{\overset{|}{C}}}\overset{}{\underset{COOR^3}{}}} \xrightarrow[\text{(ii) Reducing reagent}]{\text{(i) O}_3} \underset{(12)}{\overset{R^1}{\underset{O}{\overset{|}{\bigsqcup}}}\overset{S-R^2}{\underset{N}{\bigsqcup}}\overset{CH_3}{\underset{COOR^3}{\overset{|}{C}}\overset{}{\underset{OH}{}}}}$$

| Reaction number | $R^1$ (11) | $R^2$ | $R^3$ | (mg) | Solvent (ml) | Temperature (°C.) | Reducing reagent (ml) | (12) Crop (mg) | Yield (%) |
|---|---|---|---|---|---|---|---|---|---|
| 8 | PhOCH₂C(O)NH— | —S-(benzothiazolyl, tetrahydro) | —CHPh₂ | 1000 | CH₂Cl₂ + CH₃OH 50 + 20 | d.a. | CH₃SCH₃ 5 | 960 | 96 |
| 9 | PhOCH₂C(O)NH— | —S-(benzothiazolyl, tetrahydro) | —CH₂CCl₃ | 2500 | CH₂Cl₂ + CH₃OH 250 + 50 | −65 | CH₃SCH₃ 14 | 1670 | 66 |
| 10 | PhCH₂C(O)NH— | —S-(benzothiazolyl, tetrahydro) | —CH₂CCl₃ | 8200 | CH₂Cl₂ 500 | d.a. | CH₃SCH₃ 8 | 7100 | 86.3 |
| 11 | PhOCH₂C(O)NH— | —S-(benzothiazolyl, tetrahydro) | —CH₂CCl₃ | 1300 | CH₂Cl₂ + MeOH 65 + 13 | d.a. | NaHSO₃ 0.21 g | (II) 805; α-(1,1-dimethoxyethyl)derivative 250 | 61.7; 17.9 |
| 12 | PhOCH₂C(O)NH— | —S-(benzothiazolyl, tetrahydro) | —CH₂CCl₃ | 1300 | CH₂Cl₂ + MeOH 65 + 13 | d.a. | SO₂ 0.21 g | (II) 770; α-(1,1-dimethoxyethyl)derivative 290 | 59.1; 20.8 |

TABLE VI

Physical constants of $$\underset{(12)}{\overset{R^1}{\underset{O}{\overset{|}{\bigsqcup}}}\overset{S-R^2}{\underset{N}{\bigsqcup}}\overset{CH_3}{\underset{COOR^3}{\overset{|}{C}}\overset{}{\underset{OH}{}}}}$$

| No. | $R^1$ | $R^2$ | $R^3$ | mp. | IR: $\nu_{max}^{CHCl_3}$ (cm$^{-1}$) | NMR: $\delta^{CDCl_3}$ (6OMe) (Numbers in parentheses show coupling constants: cps) |
|---|---|---|---|---|---|---|
| 1 | phthalimido (benzene-fused N(CO)₂) | —COCH₃ | —CH₃ | 178–183° C. | 1786,1772, 1725,1662, 1618. | 2.27s3H,2.33s3H,3.86s3H, 5.77d(5)1H,6.12d(5)1H, 7.75m4H,12.3s1H. |
| 2 | PhCCH₂C(O)NH— | —COCH₃ | —CH₂C₆H₄NO₂ | Foam | 3428,1785, 1700,1608. | 2.26s3H,2.30s3H,4.55s2H, 5.2q1H,5.32s2H,5.93d(5)1H, 6.9–8.4mlOH,12.17s1H. |
| 3 | PhCCH₂C(O)NH— | —COCH₃ | —CHPh₂ | Foam | 3420,1770, 1690,1480. | 2.18s3H,2.23s3H,4.55s2H, 5.13–5.38q1H,5.93d(4.5)1H, 6.80–7.47m7H,12.23s1M. |
| 4 | PhCCH₂C(O)NH— | —COCH₃ | —CHCCl₃ | Powder | 3430,1780, 1690. | 2.27s6H,4.53s2H,4.74 + 4.86ABq(12)2H,5.51–5.37m1M, 6.02d(5)1H,6.77–7.30m5H, 11.81s1M. |
| 5 | PhCCH₂C(O)NH— | —COCCH₂-(cyclopropyl) | —CH₂C₆H₄NO₂ | Oil | 3440,1780, 1713,1667, 1608. | 0.1–1.33m5H,2.24s3H,3.96d(7)2H, 4.50s2H,5.10sm1F,5.20s2H, 5.74d(5)1M,6.70–8.14s9H, 12,10s1M. |

TABLE VI-continued

Physical constants of $$\text{(structure 12)}$$

with $R^1$, $S-R^2$ on azetidinone ring, $N$-substituent $C(CH_3)(OH)COOR^3$

| No. | $R^1$ | $R^2$ | $R^3$ | mp. | IR: $\nu_{max}^{CHCl_3}$ (cm$^{-1}$) | NMR: $\delta^{CDCl_3}$ (6OMe) (Numbers in parentheses show coupling constants: cps) |
|---|---|---|---|---|---|---|
| 6 | PhCCH$_2$CN— (with C=O, H) | —CH$_2$COC$_4$H$_9^{(t)}$ | —CH$_2$C$_6$H$_4$NO$_2$ | 56–58° C. | 3386,1777, 1729,1694, 1670. | 1.40s9H,2.23s3H,3.02q2H, 4.60s2H,5.35s2H,5.28–5.45m 2H,6.75–8.30m1OH,12.17s1M. |
| 7 | PhCCH$_2$CN— | —S-benzothiazolyl | —CH$_2$C$_6$H$_4$NO$_2$ | Oil | 3430,1778, 1686,1602. | 2.35s3H,4.55s2H,4.87–5.37m3H, 5.42d(4.5)1H,6.75– 7.97m13H,12.14s1M. |
| 8 | PhCCH$_2$CN— | —S-benzothiazolyl | —CHPh$_2$ | Powder | 3430,1779, 1690. | 2.30s3H,4.58s2H,5.13dd(5:8)1H, 5.43s(5)1H,6.9–8.0m 21H,12.25s1M. |
| 9 | PhCCH$_2$CN— | —S-benzothiazolyl | —CH$_2$CCl$_3$ | 130–132° C. | 3440,1781, 1690. | 2.40s3H,4.62s2H,4.68ABq2H, 5.15dd(5:8)1H,5.63d(3) 1H,6.8–8.0m1OH,11.8s1M. |
| 10 | PhCH$_2$CN— | —S-benzothiazolyl | —CH$_2$CCl$_3$ | Powder | 3430,1772, 1668,1602. | 2.40s3H,3.72s2H,4.47 + 4.73ABq(12)2H,4.87dd(5:8)1H, 5.52d(5)1H,6.40d(8)1M, 7.17–7.93m9H,11.73s1M. |
| 11 | PhCCH$_2$CN— | —S-benzothiazolyl | —CH$_2$CCl$_3$ | 116–119° C. | 3425,1784, 1762,1693. | 1.63s3H,3.29s6H,4.45a2H, 4.58 + 4.79ABq(14)2H,4.79m1H, 5.47–5.71m2H,6.60–7.87m1OH. | s-(1,1-dimethoxyethyl)derivative

EXAMPLE 4-IV

To a solution of α-[4-substituted ($R^2$) thio-3-substituted amino ($R^1$)-2-oxoazetidin-1-yl]-α-isopropenylacetate ester ($R^3$) in a solvent is introduced ozone under cooling. After the gas at the outlet makes potassium iodide starch paper blue, introduction of ozone is ceased, and excess ozone is removed by introduction of nitrogen gas. Reducing agent is added to the reaction mixture and let react for 10 to 30 minutes. After the reduction, the solvent is evaporated, and the residue is crystallized, or the reaction mixture is filtered through a layer of silica gel, and the filtrate is evaporated to give α-[4-substituted thio-3-substituted amino-2-oxoazetidin-1-yl]α-(1-hydroxyethylidene)acetic acid ester.

The reaction conditions are shown in Table V, and the physical constants of the products are shown in Table VI.

EXAMPLE 5-IV

According to a procedure similar to that of Example 4, the following 4-substituted thio-3-substituted amino-2-oxo-α-(1-hydroxyethylidene or acetyl)azetidine-1-acetic acid esters are prepared from the corresponding α-isopropenylazetidine derivatives.

(1) p-methoxybenzyl α-[4-(2-methyl-1,3,4-thiadiazol-5-yl)dithio-3-(2-theienylacetamido)-2-oxoazetidin-1-yl]-α-(1-hydroxyethylidene)acetate;

(2) 2,2,2-trichloroethyl α-[4-(o-nitrophenyl)dithio-3-(2,2,2-trichloroethoxycarbonamide)-2-oxoazetidin-1-yl]-α-(1-hydroxyethylidene)acetate;

(3) diphenylmethyl α-[4-cyclopropylmethoxycarbonylthio-3-tert.butoxycarbonamido-2-oxoazetidin-1-yl]-α-(1-hydroxyethylidene)acetate;

(4) 2,2,2-trichloroethyl α-[4-acetylthio-3-(N-tertiary butoxycarbonamido-α-phenylglycinamido)-2-oxoazetidin-1-yl]-α-(1-hydroxyethylidene)-acetate;

(5) p-bromophenacyl α-[4-benzothiazol-2-yl)dithio-3-(2,2-dimethyl-3-nitroso-4-phenyl-5-oxoimidazolidin-1-yl)2-oxoazetidin-1-yl]-α-(1-hydroxyethylidene)acetate;

(6) p-nitrobenzyl α-[4-(1,3,4-thiadiazol-5-yl)dithio-3-(o-nitrobenzylideneamino)-2-oxoazetidin-1-yl]-α-(1-hydroxyethylidone)acetate;

(7) methyl α-[4-benzylidithio-3-(2,6-dimethoxybenzoylamino)-2-oxoazetidin-1-yl]-α-(1phydroxyethylidene)acetate;

(8) ethyl-α-[4-acetylthio-3-cyanoacetamido-2-oxoazetidin-1-yl]-α-(1-hydroxyethylidene)acetate;

(9) acetoxymethyl 4-acetylthio-3-(α-indanyloxycarbonyl-α-phenylacetamido)-2-oxoazetidin-1-yl]-α-(1-hydroxyethylidene)acetate; and

(10) disodium α[4-pyridithio-3-(α-sulfo-α-phenylacetamide)-2-oxoazetidin-1-yl]-α-(1-hydroxyethylidene)acetate.

What we claim is:

1. A member selected from the group consisting of (a) a compound of the formula

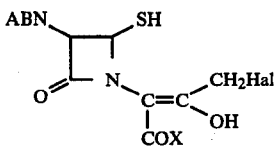

wherein A is hydrogen, B is hydrogen or an acyl group of the following formula

wherein Ar is furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl or cyclohexadienyl, each being optionally substituted by alkyl containing 1 to 3 carbon atoms, aminomethyl, hydroxy, alkoxy containing 1 to 3 carbon atoms or halogen, Q is hydrogen or methyl, and G is oxygen or sulfur or alternatively, A and B together with the nitrogen to which they are attached represent phthalimido and Hal is chlorine, bromine, iodine or fluorine, and X is OH or a carboxy protecting group containing up to 20 carbon atoms, and (b) an oxo tautomer of said compound. pg,81

2. A compound according to claim 1 of the formula

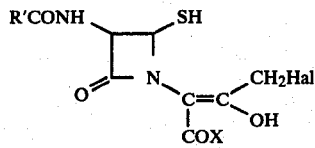

wherein Hal and X are as defined in claim 1 and R' is benzyl or phenoxymethyl.

3. A compound according to claim 1 wherein ABN is a phthalimido; X is a methoxy; and Hal is a bromine.

4. A compound according to claim 1 wherein ABN is a phenoxyacetamido; Hal is a bromine; and X is a p-nitrobenzyloxy, 2,2,2-trichloroethoxy, benzyloxy or diphenylmethoxy.

5. A compound according to claim 1 wherein ABN is a phenylacetamido; Hal is a bromine; and X is a p-nitrobenzyloxy, 2,2,2-trichloroethoxy, benzyloxy or benzhydryloxy.

6. A compound according to claim 1 wherein ABN is a phenoxyacetamido; X is a p-nitrobenzyloxy; and Hal is a chlorine.

* * * * *